(12) United States Patent
Jin et al.

(10) Patent No.: US 11,110,037 B2
(45) Date of Patent: Sep. 7, 2021

(54) METHODS AND COMPOSITIONS TO STABILIZE A NANOGEL AND DENTAL COMPOSITIONS THEREFROM

(71) Applicant: DENTSPLY SIRONA Inc., York, PA (US)

(72) Inventors: Xiaoming Jin, Middletown, DE (US); Bassam Usta, Wilmington, DE (US); Christian Scheufler, Engen (DE); Joachim E. Klee, Radolfzell (DE); Thomas Tigges, Constance (DE); Kira Neuhaus, Constance (DE); Jörg Brenneisen, Constance (DE); Hui Lu, Magnolia, DE (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 16/554,695

(22) Filed: Aug. 29, 2019

(65) Prior Publication Data

US 2020/0069530 A1    Mar. 5, 2020

Related U.S. Application Data

(60) Provisional application No. 62/769,636, filed on Nov. 20, 2018, provisional application No. 62/724,230, filed on Aug. 29, 2018.

(51) Int. Cl.
*A61K 6/17*    (2020.01)
*C08L 33/14*   (2006.01)
*A61K 6/887*   (2020.01)

(52) U.S. Cl.
CPC .............. *A61K 6/17* (2020.01); *A61K 6/887* (2020.01); *C08L 33/14* (2013.01)

(58) Field of Classification Search
None
See application file for complete search history.

(56) References Cited

U.S. PATENT DOCUMENTS

| | | | |
|---|---|---|---|
| 6,713,584 B1 * | 3/2004 | Chisholm | ......... C08F 222/1006 526/329.7 |
| 9,138,383 B1 | 9/2015 | Stansbury | |
| 9,845,415 B2 | 12/2017 | Stansbury | |
| 10,117,962 B2 * | 11/2018 | Kaikkonen | ......... A61L 24/0089 |
| 2015/0202163 A1 * | 7/2015 | Thayumanavan | ..... A61K 47/32 424/501 |

FOREIGN PATENT DOCUMENTS

WO    2015051217 A1    4/2015

OTHER PUBLICATIONS

Branched methacrylate copolymers from multifunctional comonomers: the effect of multifunctional monomer functionality on polymer architecture and properties, Slark et al., J. Matter. Chem., 2003, pp. 2711-2720 (Year: 2003).*
International Search Report; PCT/US2019/048752; Nov. 21, 2019 (completed); Nov. 28, 2019 (dated).

(Continued)

*Primary Examiner* — Peter A Salamon
(74) *Attorney, Agent, or Firm* — Dentsply Sirona Inc.

(57) ABSTRACT

The present disclosure relates to methods and compositions to stabilize a nanogel and use of such nanogel as additives in dental compositions.

40 Claims, 11 Drawing Sheets

(56) References Cited

OTHER PUBLICATIONS

Written Opinion of the International Searching Authority; PCT/US2019/048752; Nov. 21, 2019 (completed); Nov. 28, 2019 (dated).
Costello, P.A., et al: "Branched methacrylate copolymers from multifunctional monomers: chemical composition and physical architecture distributions"; Polymer, Elsevier Science Publishers B.V., GB, vol. 43, No. 2, Jun. 11, 2017, pp. 245-254.
Liu Jiancheng, et al: "A study of shrinkage stress reduction and mechanical properties of nanogel-modified resin systems", European Polymer Journal, vol. 48, No. 11, Aug. 22, 2012, pp. 1819-1828.

* cited by examiner

METHODS AND COMPOSITIONS TO STABILIZE A NANOGEL AND DENTAL COMPOSITIONS THEREFROM

FIELD OF THE DISCLOSURE

The present disclosure relates to methods and compositions to stabilize a nanogel and use of such nanogel as additives in dental compositions.

BACKGROUND OF THE DISCLOSURE

Nanogels are highly-branched discrete polymeric particles. Nanogels have been traditionally synthesized by solution copolymerization from mono-methacrylate/di-methacrylate monomers.

The major drawback in prior nanogel process has been poor copolymerization of mono-methacrylate and di-methacrylate that would result in composition shift in final Nanogel from feed composition. Overall low yield and high recovery rate of monomethacrylate has been observed. Also, there is potential formation of macrogels during polymerization as well as after vacuum drying, which would jeopardize its re-dispersibility in resins.

Chain transfer agents have been added to nanogel composition to avoid macro-gelation. U.S. Pat. No. 9,138,383 disclosed soluble nanogel polymers produced by polymerization of a monomer mixture comprising a monovinyl monomer, divinyl monomer, a chain transfer agent and an iniferter.

U.S. Pat. No. 9,845,415 disclosed a water dispersible nanogel produced by a process comprising: (i) combining a monomer mixture comprising at least one monovinyl monomer, at least one divinyl monomer, a difunctional chain transfer agent, and an initiator; and (ii) polymerizing said mixture to form the water dispersible nanogel; wherein said at least one monovinyl monomer comprises polyethoxy (10) ethyl methacrylate (E10 HEMA).

Other challenges include effectively removing all of by-products (unreacted mono-methacrylate, residual dodecane thiol (DDT) and residual solvents) to ensure quality and performance of nanogel.

Further, polymerization shrinkage and the disrupting shrinkage stress remains the major limitations of modern dental composites, and there are still tremendous needs to mitigate them in order to create advanced composite restoration with improved material integrity and well-preserved bonding, especially for the ever increasingly applied bulk-fill restorations.

Nanogels can be readily dispersed into matching monomer matrices as pre-polymerized and polymerizable additives, which contribute to lower volumetric shrinkage owing to the effective decrease of polymerizable double bonds. Furthermore, during polymerization, these monomer-swelled nanogel particles act efficiently as "stress absorber" during the rapid photopolymerization & network development.

SUMMARY OF THE DISCLOSURE

As discussed above, there is tremendous need to reduce polymerization shrinkage and the disrupting stress of dental composites in order to create advanced composite restorations.

It is an object of the present disclosure to provide a nanogel produced by the process of the present disclosure which can be used as additives in dental compositions to significantly reduce shrinkage stress and further enhance the mechanical properties of the cured product.

Further, there is a continued need for developing an effective process for forming a nanogel that would avoid macrogelation formation during the reaction process in order to stabilize a nanogel solution. This would avoid macro gelation during workup process and allow ease in re-dispersing of nanogels into resins later on. The process would be capable of removing all of the by-products for better quality of nanogel.

The present disclosure provides methods and compositions to stabilize a nanogel composition for a robust production process without macrogelation.

In a first aspect of the present disclosure, a dental composition is provided comprising a nanogel formed by a process comprising the steps of:
(a) polymerizing by a thermal polymerization a mixture comprising:
(i) at least one comonomer having one ethylenically unsaturated group,
(ii) at least one of a comonomer having two ethylenically unsaturated group and at least one comonomer having at least three ethylenically unsaturated groups
(iii) at least one chain transfer agent, and
(iv) an initiator;
at a reaction temperature to obtain a nanogel solution; and
(b) terminating the polymerization by lowering the reaction temperature and quenching the nanogel solution with a radical scavenger.

In one embodiment, provided is the use of the nanogel which is obtained by the process according to the present disclosure in order to prepare a dental composition. The dental composition may be a dental composite, a dental adhesive, a dental cement, a resin-modified glass ionomer, a vanish, a sealant, a denture material, a composite block, and a composite ink for dental 3D printing.

In another aspect of the disclosure, a method of forming a nanogel is provided. The method includes steps of:
(a) polymerizing by a thermal polymerization a mixture comprising:
(i) at least one comonomer having one ethylenically unsaturated group,
(ii) at least one of a comonomer having two ethylenically unsaturated group and at least one comonomer having at least three ethylenically unsaturated groups
(iii) at least one chain transfer agent, and
(iv) an initiator;
at a reaction temperature to obtain a nanogel solution; and
(b) terminating the polymerization by lowering the reaction temperature and quenching the nanogel solution with a radical scavenger.

In one embodiment of the method, the nanogel is essentially free of macrogel.

In another embodiment of the method, the nanogel has a hydrodynamic radius of from 2 nm to 20 nm.

In yet another embodiment of the method, the radical scavenger is present at a concentration such that the nanogel solution has a thermal stability at storage for 7 days at 25° C.

Overall, it was observed that nanogels contributed to the delayed gelation and vitrification, which resulted in not only slowing down stress development rate but also reducing the magnitude of final shrinkage stress.

The benefits are not limited to dental composites only: novel dental adhesives with nanogel additives also have potential to achieve improved durability and material properties.

DETAILED DESCRIPTION OF THE DISCLOSURE

Figure 1:
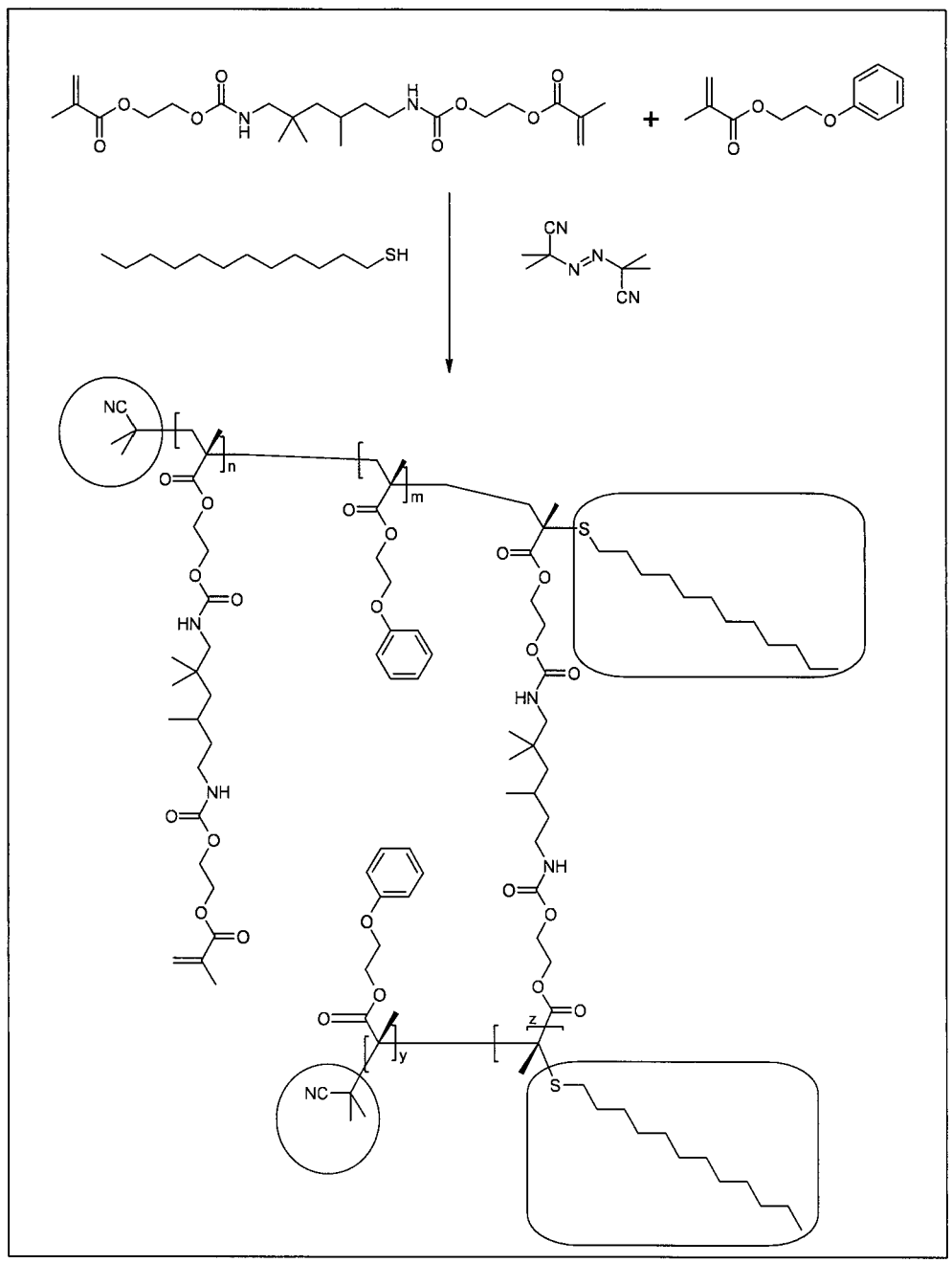
FIG. 1 depicts a scheme for synthesis of UDMA/POEMA nanogel.

The above-mentioned aspects, as well as other aspects, features, and advantages of the present disclosure are described below in connection with various embodiments, with reference made to the accompanying figures.

Some of the terms used in the present disclosure are defined below:

The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like. Alkyl groups may be substituted further with one or more substituents selected from alkenyl, alkoxy, and hydroxyl.

The term "alkylene", unless otherwise specified refers to a linear saturated divalent hydrocarbon radical of one to eighteen carbon atoms or a branched saturated divalent hydrocarbon radical of three to eighteen carbon atoms, e.g., methylene, ethylene, 2,2-dimethylethylene, propylene, 2-methylpropylene, butylene and the like, preferably methylene, ethylene, or propylene.

The term "arylene" is the divalent moiety of "aryl". The term "aryl" refers to C5-C18-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "heteroaryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridolmidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The term "aralkylene" is the divalent moiety of "aralkyl". The term "aralkyl" refers to a radical of the formula —$R^a$-aryl, where $R^a$ is an alkylene as defined above, for example, methylene, ethylene and the like. The aryl part is optionally substituted as described above for aryl group.

The term "cycloalkylene" is the divalent moiety of "cycloalkyl". The term "cycloalkyl" refers to monocyclic or polycyclic cycloalkyl radical. Examples of monocyclic acycloalkyl include cyclopropyl, cyclobutyl, cyclopentyl, cyclohexyl, cycloheptyl, and cyclooctyl. Examples of polycyclic cycloalkyl radical include, for example admantyl, norbornyl, decalinyl, 7,7-dimethyl-bicyclo[2.2.1]heptanyl, tricyclo[5.2.1.0$^{2,6}$]decyl and the like. Unless otherwise stated specifically in the specification, the term "cycloalkyl" is meant to include monocyclic or polycyclic cycloalkyl radical that are optionally substituted by one or more substituents selected from alkyl, halo, oxo or alkylene chain.

The term "cycloalkylalkylene" refers to group —R$^a$-cycloalkyl-" where R$^a$ is an alkylene as defined above, for example methylene, ethylene and the like. As used herein $C_1$-$C_5$ cycloalkylaklylene refers to a cycloalkyl linked through a $C_1$-$C_8$ alkylene group.

The term "heteroarylene" is the divalent moiety of "heteroaryl".

The term "(meth)acrylate" in the context of the present disclosure is meant to refer to the acrylate as well as to the corresponding methacrylate.

The term "(meth)acrylamide" in the context of the present disclosure is meant to include acrylamide and methacrylamide.

The present disclosure provides methods and compositions to stabilize a nanogel composition. The nanogels obtained by the process according to the present disclosure are particularly useful to prepare a dental composition. The dental composition may be a dental composite, a dental adhesive, a dental cement, a resin-modified glass ionomer, a vanish, a sealant, a denture material, a composite block, or a composite ink for dental 3D printing.

The dental composition according to the present disclosure comprises a nanogel as a component.

In an aspect of the present disclosure there is provided dental composition comprising a nanogel formed by a process comprising the steps of:
(a) polymerizing by a thermal polymerization a mixture comprising:
  (i) at least one comonomer having one ethylenically unsaturated group,
  (ii) at least one of a comonomer having two ethylenically unsaturated group and at least one comonomer having at least three ethylenically unsaturated groups
  (iii) at least one chain transfer agent, and
  (iv) an initiator;
    at a reaction temperature to obtain a nanogel solution; and
(b) terminating the polymerization by lowering the reaction temperature and quenching the nanogel solution with a radical scavenger.

The phrase "at least one of a comonomer having two ethylenically unsaturated group and at least one comonomer having at least three ethylenically unsaturated groups" should be understood to mean "only a comonomer having two ethylenically unsaturated group", "only at least one comonomer having at least three ethylenically unsaturated groups", or both "a comonomer having two ethylenically unsaturated group and at least one comonomer having at least three ethylenically unsaturated groups".

In one embodiment of the dental composition, the nanogels may be present in a concentration of from 5 to 40% wt/wt based on the total weight of the composition; alternatively in the range of from 10 to 30% wt/wt; alternatively in the range of from 10 to 25% wt/wt or any value, range, or sub-range there between, based on the total weight of the composition.

In certain embodiment of the nanogel formed by the process disclosed herein, the comonomer having one ethylenically unsaturated group is selected from the group consisting of $C_1$-$C_{12}$ alkyl(meth)acrylates, a hydroxyl alkyl (meth)acrylates, allyl ethers, an aromatic (meth)acrylates, vinylether, vinylester, vinylamine, acrylamide, methacrylamide, hydroxyl alkyl acrylamide and hydroxyl alkyl methacrylamide.

Example of $C_1$-$C_{12}$ alkyl(meth)acrylates may include but are not limited to, methyl (meth)acrylate, ethyl (meth)acrylate, isopropyl (meth)acrylate, propyl(meth)acrylate, isobutyl(meth)acrylate, hexyl(meth)acrylate, cyclo hexyl (meth)acrylate, lauryl(meth)acrylate, and isobornyl (meth)acrylate.

Examples of hydroxyl alkyl(meth)acrylates may include but are not limited to, hydroxyethyl (meth)acrylate(HEMA), polyethoxyethyl methacrylate, hydroxypropyl methacrylate and hydroxybutylmethacrylate, 6-hydroxyhexyl (meth)acrylate, and 10-hydroxydecyl(meth)acrylate.

Examples of aromatic (meth)acrylates may include but are not limited to, 2-phenoxyethyl(meth)acrylate, phenyl (meth)acrylate, benzoyl(meth)acrylate, benzyl (meth)acrylate, 2-phenylethyl (meth)acrylate, 3-phenylpropyl(meth)acrylate, 4-phenylbutyl (meth)acrylate, 4-methylphenyl (meth)acrylate, 4-methylbenzyl (meth)acrylate, and 2-(4-methoxyphenyl)ethyl methacrylate.

Examples of hydroxyalkyl acrylamide may include but are not limited to hydroxyethyl acrylamide, N-tris(hydroxymethyl)methyl)acrylamide, N-(hydroxymethyl)acrylamide or a combination thereof.

Examples of hydroxylalkyl methacrylamide include N-methylol(meth)acrylamide, hydroxyethyl(meth)acrylamide, and N,N-Bis-(2-hydroxyethyl)methacrylamide.

Examples of vinylether may include ethylvinylether, n-propyl vinylether, iso-propyl vinylether, n-butyl vinylether, iso-butyl vinylether, cyclohexyl vinylether, hydroxybutyl vinylether, cyclohexanedimethanol monovinylether, 2-ethylhexyl vinylether, dodecyl vinylether, and octadecyl vinylether.

Examples of vinylester may include but are not limited to vinylacetate, vinylpropionate, vinylbutyrate, vinylisobutyrate, vinylhexanoate, vinylstearate, neononanoate ethenyl ester, versatic acid vinylester, valeric acid vinylester, caproic acid vinylester, lauric acid vinylester, isovaleric acid vinylester, 2-ethylhexanoic vinylester, 2,2-dimethyloctanoic acid vinylester, 2-methyl-2-propyl-pentanoic acid vinylester, 4-methyl-4-butylhexanoic acid vinyl ester and vinylesters of neo acids.

Examples of a methacrylamide include (meth)acrylamide, N-methyl(meth)acrylamide, N-ethyl(meth)acrylamide, N,N-dimethyl(meth)acrylamide, N,N-diethyl(meth)acrylamide, N,N-methylethyl(meth)acrylamide, and N-(2-hydroxyethyl)methacrylamide.

Examples of acrylamide include but are not limited to N-butylacrylamide, diacetoneacrylamide, N,N-dimethylacrylamide, N,N-dibenzylacrylamide, N-ethylacrylamide, N-(2-hydroxyethyl)acrylamide, and N-methyl-N-(2-hydroxyethyl)acrylamide.

In certain embodiments, the comonomer having one ethylenically unsaturated group may be present in a range of from 50 to 95 mole percent based on total moles of comonomers in the mixture; alternatively in the range of from 55 to 80 mole percent; alternatively in the range of from 65 to 75 mole percent or any value, range, or sub-range there between, based on total moles of comonomers in the mixture.

In certain embodiments of the nanogel formed by the process disclosed herein, the comonomer having two ethylenically unsaturated group comprises a compound of Formula I X—R—Y            Formula I wherein, X is (meth)acryl or (meth)acrylamide moiety;

Y is (meth)acryl, methacrylamide, allyl, vinyl ether, vinyl ester, or vinyl amine moiety;

R is direct bond or an organic moiety;

wherein the organic moiety is selected from the group consisting of unsubstituted or substituted $C_1$-$C_{18}$ alkylene, unsubstituted or substituted $C_3$-$C_8$ cycloalkylene, unsubstituted or substituted aralkylene, unsubstituted or substituted $C_1$-$C_8$ cycloalkylalkylene, unsubstituted or substituted $C_5$-$C_{18}$ arylene and unsubstituted or substituted $C_3$-$C_{18}$ heteroarylene; wherein the organic moiety may contain at least one of from $C_1$-$C_4$ alkylene, 1-7 carbonyl groups, 1-7 carboxyl groups (—(C═O)—O— or —O—(C═O)—), 1-7 amide groups (—(C═O)—NH— or —(NH—(C═O)—), 1-7 urethane groups (—NH—(C═O)—O— or —O—(C═O)—NH—), and 1-14 heteroatoms selected from oxygen, nitrogen and sulphur; and wherein each substituted organic moiety may be substituted with one or more substituent(s) selected from the group consisting of a alkyl, hydroxyl, a thiol group, —COOM, —PO$_3$M, —O—PO$_3$M$_2$ or —SO$_3$M*; wherein M and M* are independent of each other and are hydrogen atom or metal.

In a particular embodiment, the organic moiety is an unsubstituted or substituted $C_1$-$C_{18}$ alkylene, unsubstituted or substituted $C_3$-$C_7$ cycloalkylene, unsubstituted or substituted aralkylene, unsubstituted or substituted $C_1$-$C_8$ cycloalkylalkylene, unsubstituted or substituted $C_5$-$C_{18}$ arylene or unsubstituted or substituted $C_3$-$C_{18}$ heteroarylene; wherein each unsubstituted or substituted organic moiety may contain at least one of $C_1$-$C_4$ alkylene, 1-4 urethane groups (—NH—(C═O)—O— or —O—(C═O)—NH—), 1-8 oxygen atoms or nitrogen atoms; wherein each substituted organic moiety is substituted with one or more substituent(s) selected from the group consisting of a alkyl, hydroxyl, a thiol group, —COOM, —PO$_3$M, —O—PO$_3$M$_2$ or —SO$_3$M*; wherein M and M* are independent of each other and are hydrogen atom or metal.

For organic moiety, the phrase "organic moiety may contain at least one of . . . " means that the group which may be contained in the organic moiety are incorporated in the organic moiety by means of covalent bonding. For example, in UDMA, two urethane groups (—NH—(C═O)—O— or —O—(C═O)—NH—) are incorporated in the organic moiety.

In one particular embodiment, the comonomer having two ethylenically unsaturated group may be selected from the group consisting of di (meth)acrylate, allyl (meth)acrylate, di(meth)acrylamide, (meth)acrylate (meth)acrylamide, (meth) acrylate vinylester, (meth)acrylate vinylthioester, (meth)acrylate vinylamide, vinylether (meth) acrylate, vinylester (meth)acrylate, vinylamine (meth)acrylate, allyl (meth)acrylamide, (meth)acrylamide vinyl ester, (meth) acrylamide vinylthioester, vinylether (meth)acrylamide and vinylamine (meth)acrylamide.

Examples of a comonomer having two ethylenically unsaturated groups may include but are not limited to ethyleneglycol diacrylate, ethyleneglycol dimethacrylate, diethyleneglycoldi(meth)acrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), butyleneglycoldi(meth)acrylate, tetraethyleneglycoldi(meth)acrylate, neopentyl glycol diacrylate, neopentylglycol dimethacrylate, 1,6-hexanediol di(meth)acrylate, 1,10-decanediol di(meth)acrylate, pentaerythritol di(meth)acrylate, 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4), (UDMA), N,N'-ethylenebis(meth)acrylamide; N,N'-propylenebis(meth)acrylamide; N,N'-butylenebis (meth)acrylamide; N,N'-pentamethylenebis(meth)acrylamide; N,N'-hexamethylenebis(meth)acrylamide, dimethylene ether diacrylamide, dimethylene ether dimethacrylamide, methylenebisacrylamide, and methylenebismethacrylamide, compounds of Formula

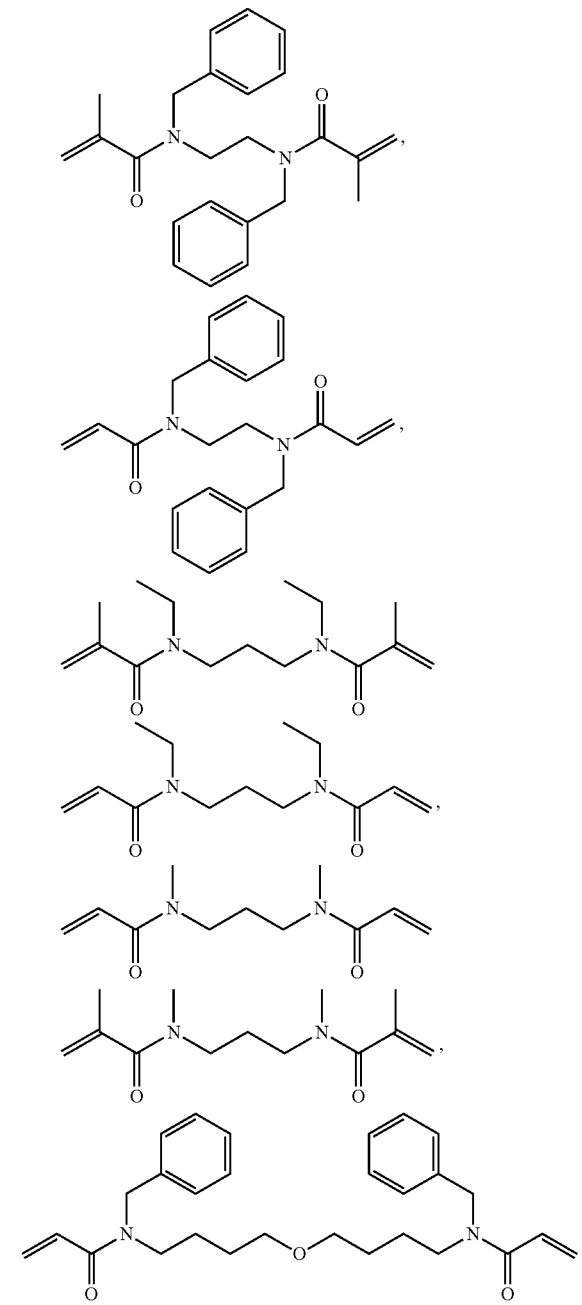

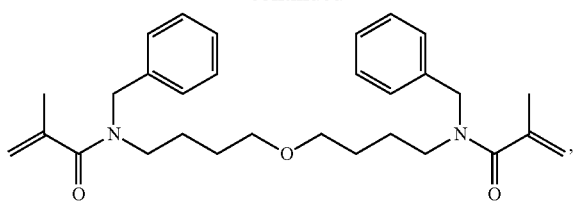
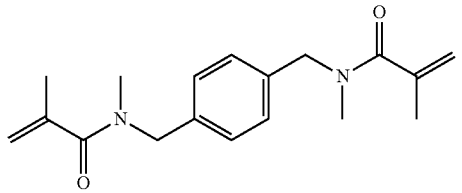
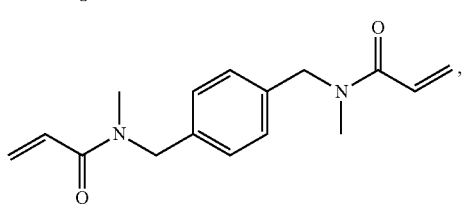
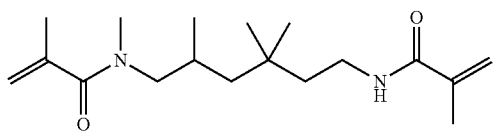
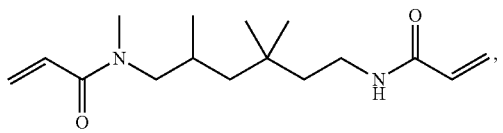
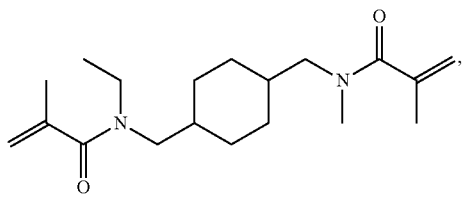
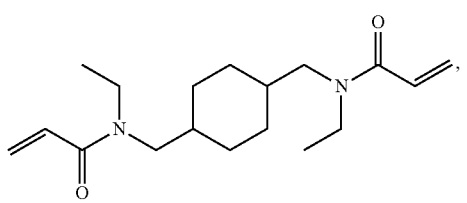
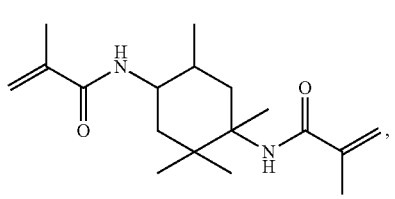
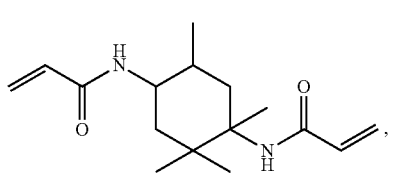

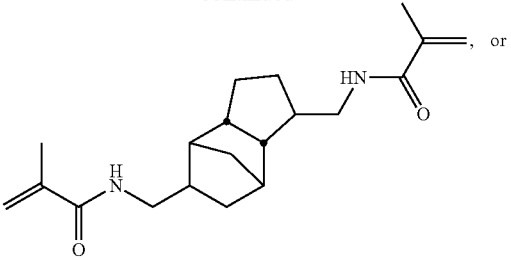

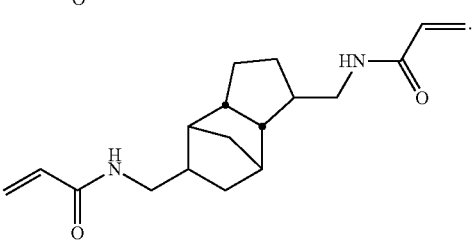

In certain embodiments, the comonomer having two ethylenically unsaturated group is present in a range of from 5 to 50 mole percent based on total moles of comonomers in the mixture; alternatively in the range of from 10 to 40 mole percent; alternatively in the range of from 20 to 30 mole percent or any value, range, or sub-range there between, based on total moles of comonomers in the mixture.

In certain embodiments of the nanogel formed by the process disclosed herein, the comonomer having at least three ethylenically unsaturated groups is selected from the group consisting of trimethylolpropane tri(meth)acrylate, pentaerythritol triacrylate, and pentaerythritol tetra-acrylate, dipentaerythritol hexaacrylate and N,N'-Bisacryloyl-N,N'-bisallyl-1,4-but-2-endiamine (BAABE).

In certain embodiments, the comonomer having at least three ethylenically unsaturated groups is present in a range of from 1 to 30 mole percent based on total moles of comonomers in the mixture; alternatively in the range of from 2 to 20 mole percent; alternatively in the range of from 5 to 15 mole percent or any value, range, or sub-range there between, based on total moles of comonomers in the mixture.

In certain embodiments of the nanogel formed by the process disclosed herein, at least one chain transfer agent may be included.

The chain transfer agent may be used to afford shorter polymer chains that delays macrogel formation. The chain transfer agent may be RSH, wherein R is a linear or branched alkyl having from 3 to 20 carbon atoms. Examples of a chain transfer agent may include propyl mercaptan, butyl mercaptan, hexyl mercaptan, 1-dodecanethiol, mercaptoethanol and combinations thereof.

The amount of at least one chain transfer agent is present in a concentration of from 5 to 50% mol/mol based on total moles of comonomers in the mixture; alternatively in the range of from 10 to 40% mol/mol; alternatively in the range of from 20 to 30% mol/mol or any value, range, or sub-range there between, based on the total moles of comonomers in the mixture.

In certain embodiments of the nanogel formed by the process disclosed herein, an initiator may be included.

The thermal polymerization of the comonomers may be initiated by decomposition of initiator. The initiator may be selected from at least one of organic peroxides and azo compounds.

In certain embodiments, the initiator is selected from the group consisting of benzoyl peroxide, 2,2-azobis-(2-methylpropionitrile) and 2,2-azobis-(2-methylbutyronitrile). In a preferred embodiment, initiator is azobis (isobutryonitrile).

The thermal initiator may be present in a concentration of from 0.5 to 5.0% wt/wt based on based on total weight of comonomers in the mixture. Alternatively in the range of from 0.5 to 3.0% w/w; alternatively in the range of from 1.0 to 2.0% w/w or any value, range, or sub-range there between, based on a total weight of comonomers in the mixture.

In certain embodiments of the nanogel formed by the process disclosed herein, a radical scavenger may be included.

The radical scavenger may be added at the end of the conventional radical polymerization to terminate the polymerization. This would eliminate all the radical species within the resulting polymers as non-active species. A stable nanogel system would be achieved to allow its subsequent exposure to heat and vacuum, without causing any unwanted macrogelation.

The radical scavenger is present in an amount of at least 0.05% wt/wt and up to 2.5% wt/wt; or the radical scavenger may be present in an amount of at least 0.1% and up to 1.5% wt/wt based on a total weight of comonomers in the mixture. Alternatively, the radical scavenger may be present in an amount of at least 0.1% wt/wt based on total initiator used in nanogel or 10-50% wt/wt based on total initiator used in nanogel.

Examples of radical scavengers may include but are not limited to TEMPO, substituted TEMPO and polychlorinated triphenylmethyl radicals, phenalenyls, cyclopentadienyls, and other carbon centered radicals, a nitroxide radical, di-tert-alkyliminoxyls, delocalized radicals containing a hydrazyl unit, metal-coordinated phenoxy radicals, and stable radicals containing a thiazyl unit or stable radicals of a heavy p-block elements.

TEMPO is 2,2,6,6-tetramethylpiperdine-1-oxyl. Structure of TEMPO and representative examples of substituted TEMPO are depicted below:

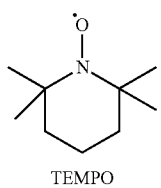

TEMPO

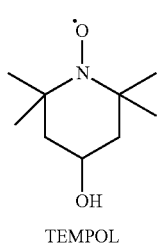

TEMPOL

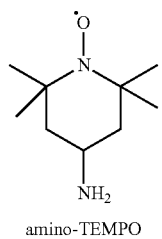

amino-TEMPO

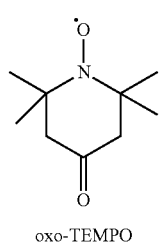

oxo-TEMPO

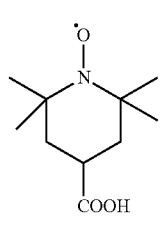

carboxy-TEMPO

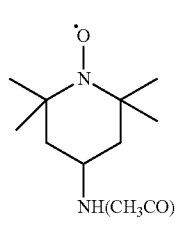

N-acetylo-TEMPO

Examples of polychlorinated triphenylmethyl radicals may include following:

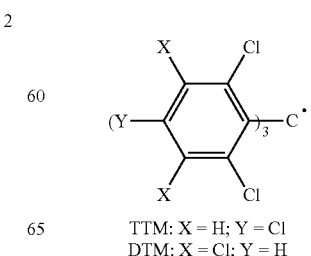

TTM: X = H; Y = Cl
DTM: X = Cl; Y = H

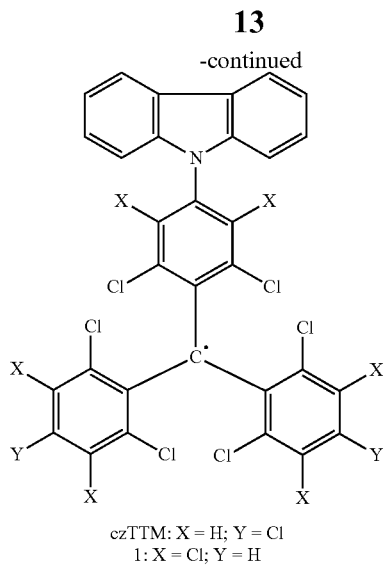

czTTM: X = H; Y = Cl
1: X = Cl; Y = H

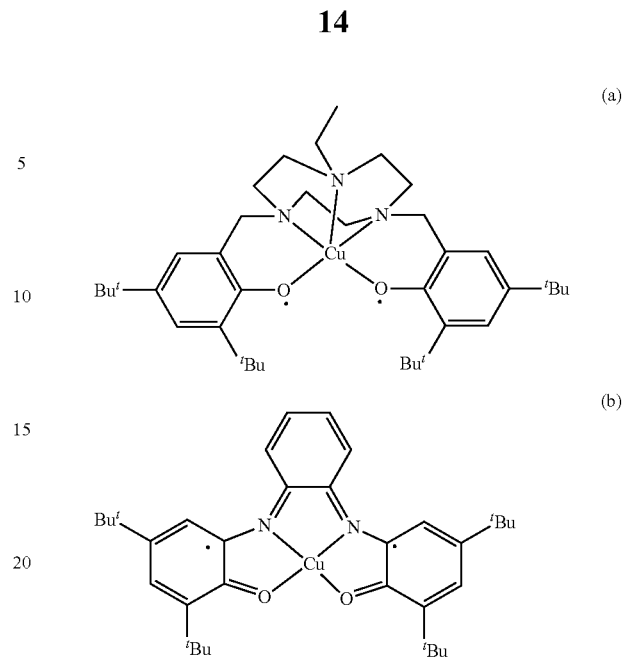

Phenalenyls are structures depicted below:

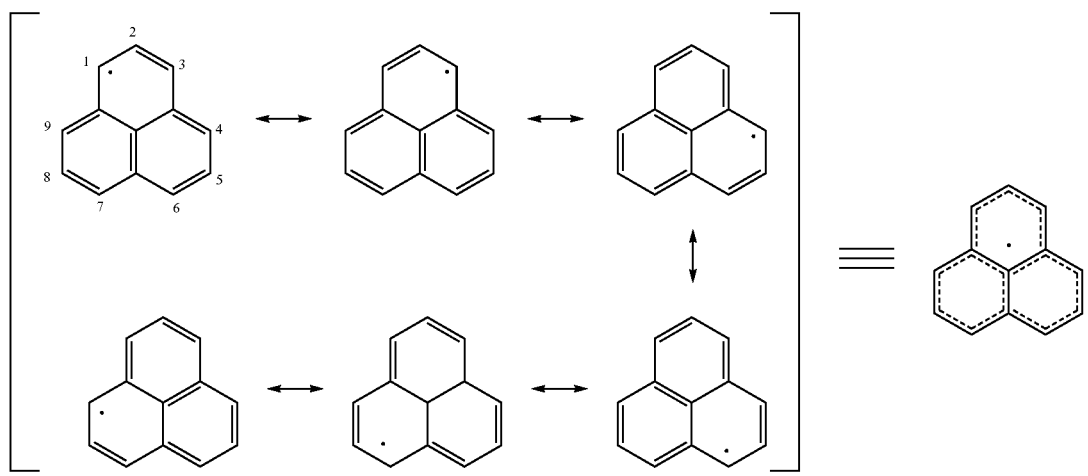

Typical Structure of Cyclopentadienyl Radical include

Di-tert-butyliminoxyl radical include structure of Formula

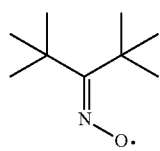

Metal-Coordinated Phenoxy Radicals may include structures depicted below:

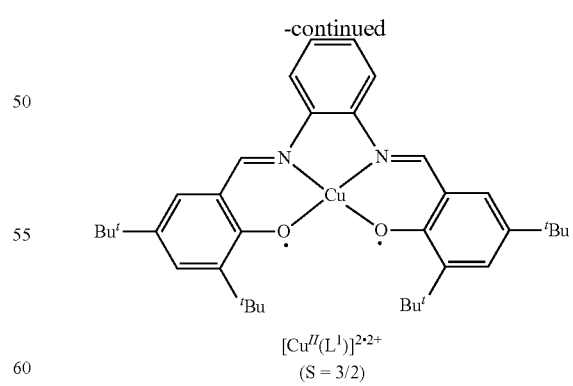

In one embodiment of the nanogel formed by the process of the present disclosure, the nanogel is essentially free of macrogel.

The nanogel formed by the process of the present disclosure has a hydrodynamic radius below 50 nm; alternatively, the hydrodynamic radius of the nanogel is in a range of from 1 nm to 50 nm, more preferably, in a range of from 2 nm to 20 nm.

In one aspect of the present disclosure there is provided a method of forming a nanogel; the method comprising steps of:
(a) polymerizing by a thermal polymerization a mixture comprising:
(i) at least one comonomer having one ethylenically unsaturated group
(ii) at least one of a comonomer having two ethylenically unsaturated group and at least one comonomer having at least three ethylenically unsaturated groups
(iii) at least one chain transfer agent, and
(iv) an initiator;
at a reaction temperature to obtain a nanogel solution; and
(b) terminating the polymerization by lowering the reaction temperature and quenching the nanogel solution with a radical scavenger.

The thermal polymerization may be carried out using any free radical polymerization method for example solution, suspension, emulsion and bulk polymerization method.

In one embodiment of the method of forming the nanogel, a mixture of at least one comonomer having one ethylenically unsaturated group; at least one of a comonomer having two ethylenically unsaturated group and at least one comonomer having at least three ethylenically unsaturated groups, at least one chain transfer agent, and an initiator may be dissolved in a solvent.

Suitable solvents to be used in the method of preparing the nanogel herein are inert solvents. Examples of suitable solvents would be the ones in which monomers dissolve, such as dipolar aprotic solvents such as methyl ethyl ketone or methyl isobutyl ketone, ketones such as acetones, 2-butanone, or cyclohexanone, hydrocarbons such as toluene and xylene, ether such as dioxane or tetrahydrofuran. In one particular embodiment, the solvent is methyl ethyl ketone or methyl isobutyl ketone.

The amount of solvent may be present at concentration such that it minimize the formation of macrogel, which could range from 2-10 times of total weights of total comonomers.

In one embodiment of the method of forming the nanogel, the thermal polymerization may be performed at a reaction temperature of from 40° C. to 150° C.; such as from 60° C. to 120° C. or from 75° C. to 105° C.

In one embodiment of the method of forming the nanogel, the thermal polymerization may be terminated by lowering the reaction temperature and quenching the nanogel solution with a radical scavenger.

In some embodiments of termination of thermal polymerization, the reaction temperature may be lowered by cooling the nanogel solution at temperature of from −196° C. to 25° C.

In some embodiments of termination of thermal polymerization, the nanogel solution may be quenched, when the radical scavenger is added to the nanogel solution when 55-85% of the ethylenically unsaturated group in the comonomer mixture have reacted to form the nanogel. In one particular embodiment, the radical scavenger is added to the nanogel solution when 75-80% of the ethylenically unsaturated group in the comonomer mixture have reacted to form the nanogel.

In further embodiments, a method disclosed herein may further comprise precipitating the nanogel mixture after quenching with radical scavenger with a non-polar solvent. Alternatively dialyzing, the nanogel mixture against solvent using a regenerated cellulose membrane with a molecular weight cut off of 10 kDa.

The non-polar solvent used for precipitating the nanogel mixture may be pentane, hexane, n-heptane, cyclohexane, octane, or petrolether.

The solvent used for dialyzing the nanogel mixture may be acetone, 2-butanone, or iso-butylmethylketone.

After precipitating or dialyzing the nanogel mixture, the solvent may be removed under vacuum to form nanogel.

The nanogels formed by the process of present disclosure can be re-dispersed to give a stable nanoparticle suspension in appropriate solvent. For example, the nanogel can be easily re-dispersed into solvent selected from the group consisting of acetone, toluene or methyl ethyl ketone to provide a suitable suspension.

The dental compositions disclosed herein may contain polymerizable resin, a polymerization initiator and an additional filler.

Polymerizable Resin

In one embodiment of the dental composition, the polymerizable resin may be present in an amount of from about 1 weight percent to about 95 weight percent of the dental composition.

Polymerizable resin may be selected from the group consisting of acrylates, methacrylates, ethylenically unsaturated compounds, carboxyl group-containing unsaturated monomers, $C_{2-8}$ hydroxyl alkyl esters of (meth)acrylic acid, $C_{1-24}$ alkyl esters or cycloalkyl esters of (meth)acrylic acid, $C_{2-18}$ alkoxyalkyl esters of (meth)acrylic acid, olefins or diene compounds, monoesters/diesters, monoethers, adducts, TPH resin, SDR Resin and/or BPA-free resins.

Examples of specific acrylate resins include, but are not limited to, methyl acrylate, ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethyleneglycol diacrylate, polyethyleneglycol diacrylate, neopentyl glycol diacrylate, trimethylolpropane triacrylate, mono-, di-, tri-acrylate, mono-, di-, tri-, and tetra-acrylates of pentaerythritol and dipentaerythritol, 1,3-butanediol diacrylate, 1,4-butanedioldiacrylate, 1,6-hexane diol diacrylate, 2,2'-bis[3(4-phenoxy)-2-hydroxypropane-1-acrylate]propane, 2,2'-bis(4-acryloxyphenyl)propane, 2,2' bis[4(2-hydroxy-3-acryloxyphenyl)propane, 2,2'-bis(4-acryloxyethoxyphenyl)propane, 2,2'-bis(4-acryloxypropoxyphenyl)propane, 2,2'-bis(4-acryloxydiethoxyphenyl)propane, and dipentaerythritol pentaacrylate esters.

Examples of specific conventional methacrylate resins include, but are not limited to, methyl methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (Bis-GMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentaerythritol and dipentaerythritol, 1,3-butanediol dimethacrylate, 1,4-butanediol dimethacrylate, Bis[2-(methacryloyloxy)ethyl] phosphate (BisMEP),1,6-hexanediol dimethacrylate, 2,2'-bis(4-methacryloxyphenyl)propane, 2,2'-bis[4(2-hydroxy-3-methacryloxy-phenyl)]propane, 2,2'-bis(4-methacryloxyethoxyphenyl)propane, 2,2'-bis(4-methacryloxypropoxyphenyl)propane, 2,2'-bis(4- methacryloxydiethoxyphenyl)propane, and 2,2'-bis[3(4-phenoxy)-2-hydroxypropane-1-methacrylate]propane.

Examples of ethylenically unsaturated compounds include, but are not limited to, acrylic acid esters, methacrylic acid esters, hydroxy-functional acrylic acid esters, hydroxy-functional methacrylic acid esters, halogen and hydroxy containing methacrylic acid esters and combinations thereof. Such free radically polymerizable compounds include n-, -, sec-, or t-butyl methacrylate, hexyl methacrylate, 2-ethylhexyl methacrylate, octylmethacrylate, decyl methacrylate, lauryl methacrylate, cyclohexyl methacrylate, stearyl methacrylate, allyl(meth)acrylate, glycerol tri(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; urethane modified BisGMA resin, the bis-(meth)acrylates of polyethylene glycols, and chlorine-, bromine-, fluorine-, and hydroxyl group containing monomers, for example, 3-chloro-2-hydroxylpropyl (meth)acrylate.

Examples of carboxyl group-containing unsaturated monomers include but are not limited to, such as acrylic acid, methacrylic acid, crotonic acid, itaconic acid, maleic acid, and fumaric acid.

Examples of $C_{2-8}$ hydroxyl alkyl esters of (meth)acrylic acid include but are not limited to 2-hydroxylethyl (meth)acrylate, 2-hydroxypropyl (meth)acrylate, 3-hydroxypropyl (meth)acrylate, and hydroxybutyl (meth)acrylate.

Examples of $C_{2-18}$ alkoxyalkyl esters of (meth)acrylic acid include, but are not limited to, methoxybutyl methacrylate, methoxyethyl methacrylate, ethoxyethyl methacrylate, and ethoxybutyl methacrylate.

Olefins or diene compounds include, but are not limited to, ethylene, propylene, butylene, isobutene, isoprene, chloropropene, fluorine containing olefins and vinyl chloride.

Examples of monoesters may include monoesters between a polyether polyol (e.g., polyethylene glycol, polypropylene glycol or polybutylene glycol) and an unsaturated carboxylic acid (preferably methacrylic acid), monoesters or diesters between an acid anhydride group-containing unsaturated compounds (e.g., maleic anhydride or itaconic anhydride) and a glycol (e.g. ethylene glycol, 1,6-hexanediol or neopentyl glycol).

Example of monoethers may include monoethers between a polyether polyol (e.g., polyethylene glycol, polypropylene glycol or polybutylene glycol) and a hydroxyl group-containing unsaturated monomers (e.g., 2-hydroxyl methacrylate).

Examples of adducts may include, but are not limited to, adducts between an unsaturated carboxylic acid and a monoepoxy compound; adducts between glycidyl (meth)acrylates (preferably methacrylate) and a monobasic acid (e.g., acetic acid, propionic acid, p-t-butylbenzonic acid or a fatty acid).

Initiators

Initiators are often used in chain-growth polymerization such as radical polymerization to regulate initiation by heat or light.

Thermal polymerization initiators are compounds that generate radicals or cations upon exposure to heat. For example, azo compounds such as 2,2'-azobis(isobutyronitrile) (AIBN) and organic peroxides such as benzoyl peroxide (BPO) are well-known thermal radical initiators, and benzenesulfonic acid esters and alkylsulfonium salts have been developed as thermal cation initiators. Organic and inorganic compounds can be used to generate radicals that initiate polymerizations. Radicals may be generated by thermal or ambient redox conditions. Decomposition rates for some initiators vary with pH and the presence of amines.

Additional free radical initiators may include organic photoinitiators. Suitable photoinitiators include Type I and Type II. They can be used independently or as mixture of different photoinitiators plus additional co-initiators. Suitable photosensitizers may include monoketones and diketones (e.g. alpha diketones) that absorb some light within a range of about 300 nm to about 800 nm (such as, about 400 nm to about 500 nm) such as camphorquinone, benzil, furil, 3,3,6,6-tetramethylcyclohexanedione, phenanthraquinone and other cyclic alpha diketones. In embodiments, the initiator is camphorquinone. Examples of electron donor compounds include substituted amines, e.g., ethyl 4-(N,N-dimethylamino)benzoate as the accelerator.

Other suitable photoinitiators for polymerizing free radically photopolymerizable compositions may include the class of phosphine oxides that typically have a functional wavelength range of about 380 nm to about 1200 nm. In embodiments, phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm may include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). bis(2,4,6-trimethylbenzoyl) phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X).

In one embodiment of the dental composition, the initiator may be present in an amount of from 0.05 weight percent to about 5 weight percent of the dental composition.

Fillers

The dental composition of the present disclosure may include fillers.

Examples of suitable filler particles include, but are not limited to, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The filler particles used in the composition disclosed herein may be surface treated before they are blended with organic compounds. The surface treatment using silane coupling agents or other compounds are beneficial as they enable the filler particles to be more uniformly dispersed in the organic resin matrix, and also improve physical and mechanical properties. Suitable silane coupling agents include 3-methacryloxypropyltrimethoxysilane, methacryloxyoctyltrimethoxysilane, styrylethyltrimethoxysilane, 3-mercaptopropyltrimethoxysilane, and mixtures thereof.

The filler particles can have a particle size of from about 0.002 microns to about 25 microns. In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). The concentration of micron-size glass particles can range from about 50 weight percent to about 75 weight percent of the dental composition, and the nano-size filler particles can range from about 1 weight percent to about 20 weight percent of the dental composition.

The dental composition of the present disclosure may include a filler material in an amount from about 5 to about 95 percent by weight.

In formulated compositions, additional additives may be optionally included: ultra-violet stabilizers, fluorescent agents, opalescent agents, pigments, viscosity modifiers, fluoride-releasing agents, polymerization inhibitors, and the like. Typical polymerization inhibitors for a free radical system may include hydroquinone monomethyl ether (MEHQ), butylated hydroxytoluene (BHT), tertiary butyl hydro quinone (TBHQ), hydroquinone, phenol, butyl hydroxyaniline, and the like. The inhibitors act as free radical scavengers to trap free radicals in the composition and to extend the shelf life stability of the composition. The polymerization inhibitors, if present, may be present in amounts of from about 0.001 weight percent to about 1.5 weight percent of the dental composition, such as from about 0.005 weight percent to about 1.1 weight percent or from about 0.01 weight percent to about 0.08 weight percent of the dental composition. The composition may include one or more polymerization inhibitors.

The disclosure discussed herein is further illustrated by the nanogel compositions, dental compositions described in the following Examples, but these Examples should not be construed as limiting the scope of the present disclosure.

EXAMPLES

Batch Reaction (Conventional Thermal Process):

Solution copolymerizations of isobornyl methacrylate (IBMA) and urethane dimethacrylate (UDMA) (70/30 mole ratio) were conducted with 20% mol of mercaptoethanol (ME) and 20% mol of 1-dodecanethiol (DDT) as chain-transfer agent. Thermal polymerizations used 1 wt % 2,2-azobisisobutyronitrile at 75-80° C. in 2-butanone (MEK) or toluene, respectively.

A variety of lab batches of nanogel based on UDMA/IBMA (30:70 molar ratio) and/or UDMA/POEMA (30:70 molar ratio) were successfully reproduced but lower yields of 50-70% consistently achieved, see examples in Table I. In addition, it was revealed that fractional macrogel could be formed along with the nanogel during the solvent removing process, though the initial precipitated nanogel could be dissolved completely. The presence of such a macrogel would negatively impact the yield and the dissolution of any resulting nanogel in a formulated resin mixture.

TABLE I

Composition and Solvent Effect on Yield and Solubility of Nanogel via Batch Process

| | Resin Composition | | | Reaction Condition | | | | | Solubility in Acetone |
|---|---|---|---|---|---|---|---|---|---|
| Nanogel | UDMA mol % | IBMA mol % | POEMA mol % | Solvent Toluene (T), Methylethylketone (MEK) | Temp. ° C. | Time min. | Conversion % | Yield % | |
| 50 g Example 1 | Esstech 30 | Aldrich 70 | 0 | T | 80 | 55 | 84 | 70 | Not all |
| 100 g Example 2 | Esstech 30 | Aldrich 70 | 0 | T | 80 | 45 | 86 | 70 | Not all |
| 100 g Example 3 | Esstech 30 | Aldrich 70 | 0 | T | 80 | 35 | 71 | 70 | Not all |
| 100 g Example 4 | Esstech 30 | Aldrich 70 | 0 | T | 80 Quenched | 30 | 76 79 | 64 | Not all |
| 100 g Example 5 | Esstech 30 | TCI 70 | 0 | T | 80 | 30 | 76 | 70 | Not all |
| 100 g Example 6 | Esstech 28.8 | 0 | 71.2 | T | 80 | 35 | 80 | N/A | macrogel |
| 100 g Example 7 | Esstech 30 | 0 | 70 | T | 80 | 25 | 68 | 74 | Not all |
| 100 g Example 8 | 25 | 0 | 75 | MEK | 75 | 50 | 67 | 62 | Yes all |

TABLE I-continued

Composition and Solvent Effect on Yield and Solubility of Nanogel via Batch Process

| Nanogel | Resin Composition | | | Reaction Condition | | | | | Solubility |
| | UDMA mol % | IBMA mol % | POEMA mol % | Solvent Toluene (T), Methylethylketone (MEK) | Temp. ° C. | Time min. | Conversion % | Yield % | in Acetone |
|---|---|---|---|---|---|---|---|---|---|
| 100 g Example 9 | 27.3 | 0 | 72.7 | MEK | 80 | 55 | 82 | 73 | Yes all |
| 100 g Example 10 | 30 | 0 | 70 | MEK | 80 | 50 | 67 | 70 | Yes all |
| 200 g Example 11 | 30 | 0 | 70 | MEK | 80 | 55 | 82 | 73 | Yes all |

Low yield was attributed due to poor copolymerization of monomethacrylate and dimethacrylate; for example, POEMA with UDMA, even though POEMA appeared to have better copolymerization than IBMA. Consequently less POEMA was incorporated into the nanogel and the actual composition of such nanogel would deviate from the feed composition of 30/70 mol/mol of UDMA/POEMA, see Table II, Example 17.

TABLE II

Resin Composition for Improved Yield and Solvent Effect on Solubility of Nanogel

| Nanogel | Resin Composition | | | Solvent Toluene (T), Methylethylketone (MEK) | Reaction Time min. | Yield % | Solubility in Acetone |
| | UDMA mol % | IBMA mol % | POEMA mol % | | | | |
|---|---|---|---|---|---|---|---|
| Example 12 | 30 | 70 | | T | 5 | 51 | Not all w/gelled residue |
| Example 13 | 30 | 70 | | T | 5 | 56 | Not all w/gelled residue |
| Example 14 | 30 | 70 | | T | 15 | 66 | Not all w/gelled residue |
| Example 15 | 30 | | 70 | T | 5 | 66 | yes/hazy |
| Example 16 | 30 | | 70 | T | 5 | 70 | yes/hazy |
| Example 17 | 40 | | 60 | T | 5 | 72 | yes/hazy |

For hexane-soluble fractions in current Nanogel Process: UDMA/IBMA vs UDMA/POEMA based on NMR analysis, following was concluded:

(i) For UDMA/IBMA (30/70, in MEK): 44.5 g (37.5% wt./wt.) of hexane-soluble liquid was collected as unreacted IBMA, IBMA oligomers and free DDT. Very little of UDMA was present.

(ii) For UDMA/POEMA (25/75, in MEK): 40.0 g (33.5% wt./wt.) of hexane-soluble liquid was collected as POEG/PODEG, unreacted POEMA, POEMA oligomers and free DDT. Very little of UDMA and no crystalline residue was found.

(a) It was estimated based on $^1$H NMR analysis, there is 12.8 g (32%) as free DDT; 27.2 g (68%) as free POEMA and/or POEMA oligomers;

(b) 12.8/13.6=94% wt./wt. of DDT was recovered; 27.2/56.8=47.9% wt./wt. of POEMA was recovered.

Thus final composition of this nanogel would be as UDMA/POEMA in 39/61 (mol/mol).

There was still issue an with the insoluble fraction in the final nanogel after drying, which was attributed to the macrogel, due to the instability of trapped free radical in nanogel. This issue needs to be resolved for ease of the subsequent workup process and ensure quality of the re-dispersion of the final nanogel in any formulated compositions. Thus, it is was proposed to introduce a chemical quenching process to such reaction systems to stabilize the nanogel and to avoid any macro gelation during the workup process. The formed nanogel would also be capable of easily re-dispersing into resins later on.

A stable radical, TEMPO, should serve well for this purpose. For a general mechanism of controlled radical polymerization via nitroxide-mediated polymerization (NMP), a growth radical should be terminated adequately. One critical aspect of NMP is that depending upon the monomer's structure nature and/or nitroxide compound, the reversibility would vary. Styrene, for example, could undertake further thermal cleavage to re-join radical polymerization, develop into controlled radical polymerization at elevated temperatures such as 110-120° C. However, such reversible processes would NOT occur in any methacrylate system unless specially designed nitroxide compounds are used. More specifically TEMPO would not work to serve for NMP towards methacrylate, though it should quench methacrylate propagating radical adequately. Therefore, TEMPO should be ideal candidate for use to stabilize nanogel.

Preparation Example 1

The following Raw materials were used:

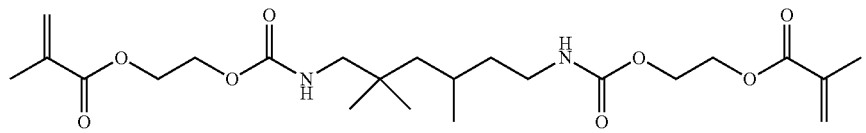

UDMA
Molecular Weight = 470.57
Molecular Formula = $C_{23}H_{38}N_2O_8$

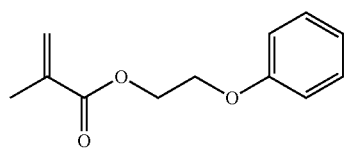

POEMA
Molecular Weight = 209.24
Molecular Formula = $C_{12}H_{14}O_3$

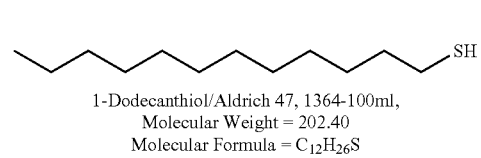

1-Dodecanethiol/Aldrich 47, 1364-100ml,
Molecular Weight = 202.40
Molecular Formula = $C_{12}H_{26}S$

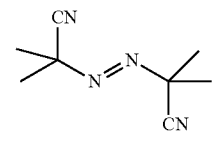

AIBN
Molecular Weight = 164.21
Molecular Formula = $C_8H_{12}N_4$

Solution copolymerizations of 2-phenylethylene glycol methacrylate (POEMA) and urethane dimethacrylate (UDMA) (70/30 mole ratio, FIG. 1) were conducted with 30% mol of 1-dodecanethiol (DDT) as chain-transfer agent. 1% wt/wt of 2, 2-azobisisobutyronitrile (AIBN) at 75-80° C. in 2-butanone (MEK) 200 g, were added respectively. Methacrylate conversion was monitored by FTIR and once the target conversion of 75-80% was achieved, the reaction solution was discharged. 0.20%, wt/wt, of TEMPO was added to such discharged solution to allow a mixing for 30 min at room temperature to form a nanogel mixture. The nanogel mixture was precipitated in 2000 mL hexane, under vigorous agitation to yield the wet nanogel. The wet nanogel was separated by decanting the hexane solution. It was further dried under reduced pressure for at least 12 hours. Dried nanogel was collected and the residue in the dry flask could be completely dissolved in acetone, which is good indicator of effective TEMPO-quenching process occurred. Furthermore such TEMPO-stabilized nanogel should be readily redissolved in acetone or other resin blends.

Figure 2:
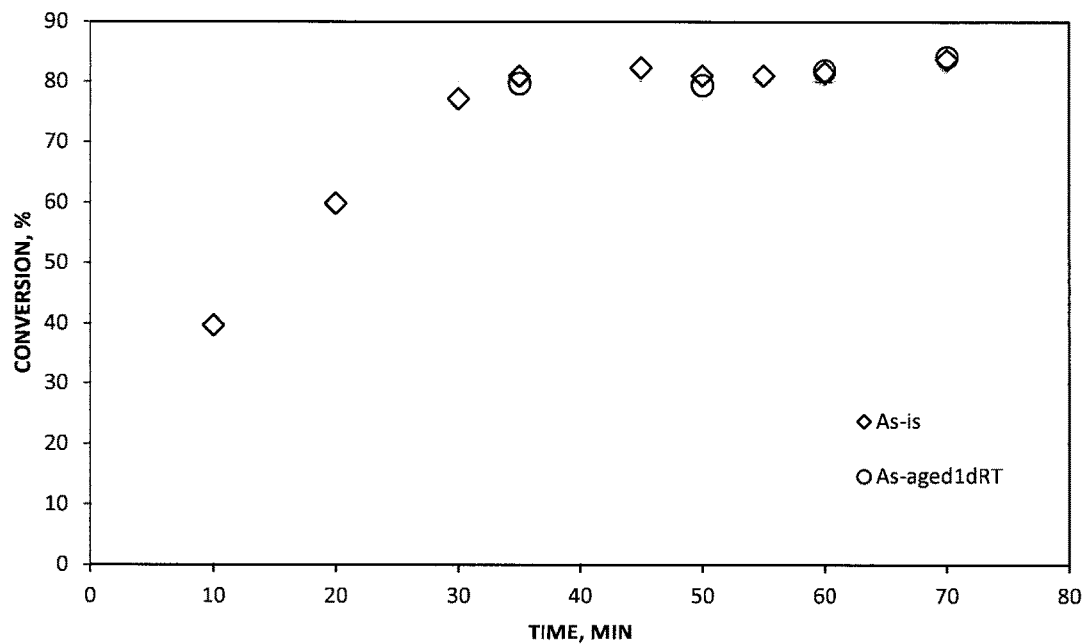
FIG. 2 shows methacrylate (MA) conversion in TEMPO-stabilized nanogel process (ZZ1-85 with TEMPO 0.09% wt/wt of total weight of monomers @ 80° C.).

As depicted in FIG. 2, during the normal free radical polymerization process, the total methacrylate conversion steadily increases. The reaction solution was discharged when the conversion reached 75% and no further increase in conversion was found from as discharged and/or as aged 1 dRT, which should suggest the TEMPO is very effective to terminate the growth radical permanently.

Figure 3:
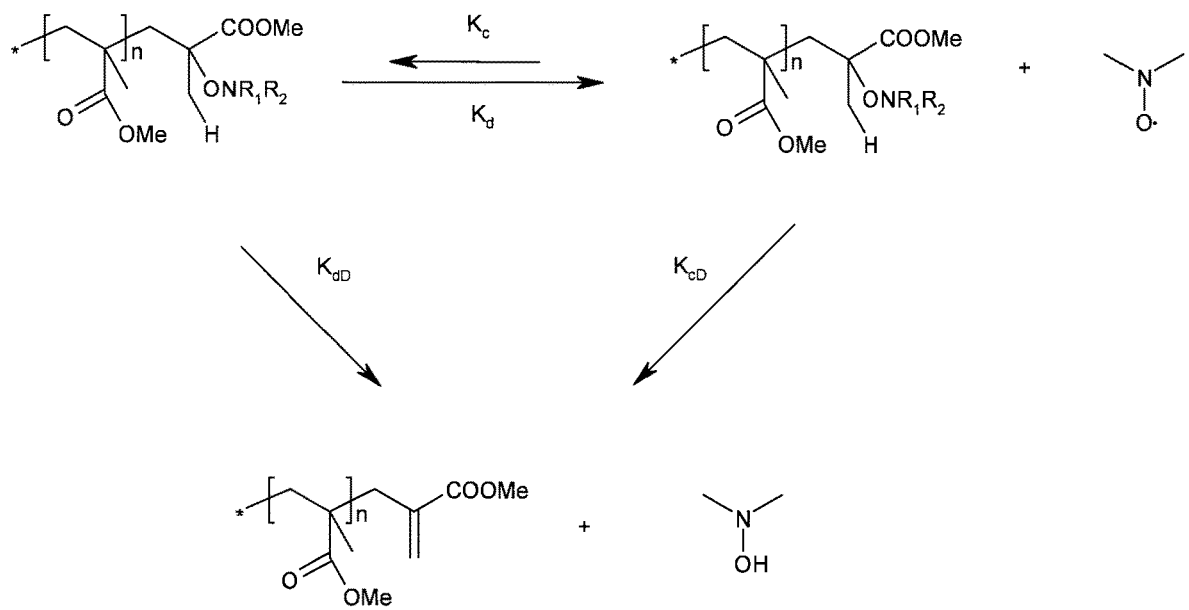
FIG. 3 depicts general mechanism for side reaction in methacrylate-nitroxide system.
Figure 4:
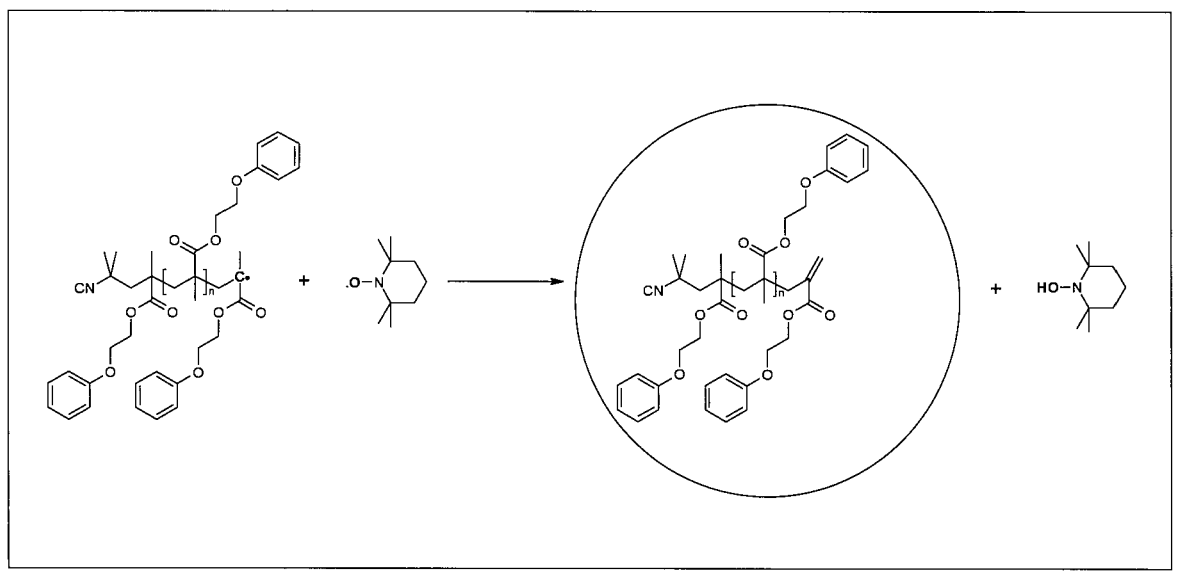
FIG. 4 depicts possible side-reaction from TEMPO-quenched nanogel at elevated temperatures.
Figure 6:
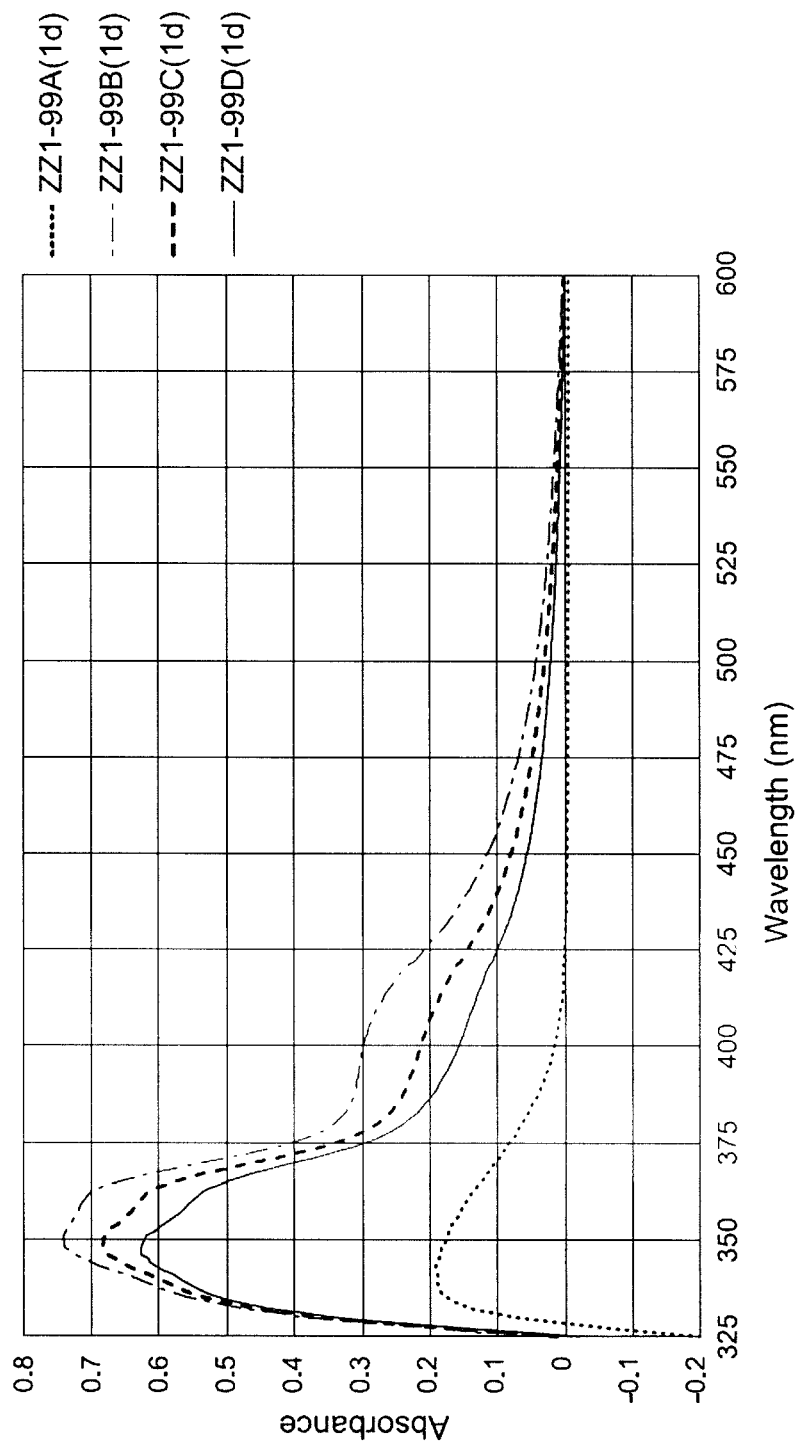
FIG. 6 shows thermal aging effects on UV Spectra of TEMPO-stabilized MEK solution of nanogel/ZZ1-99 with variable TEMPO (@ 40° C., A: 0%; B: 0.20%; C: 0.16%; D: 0.12%, wt/wt of total weight of monomers).
Figure 7:
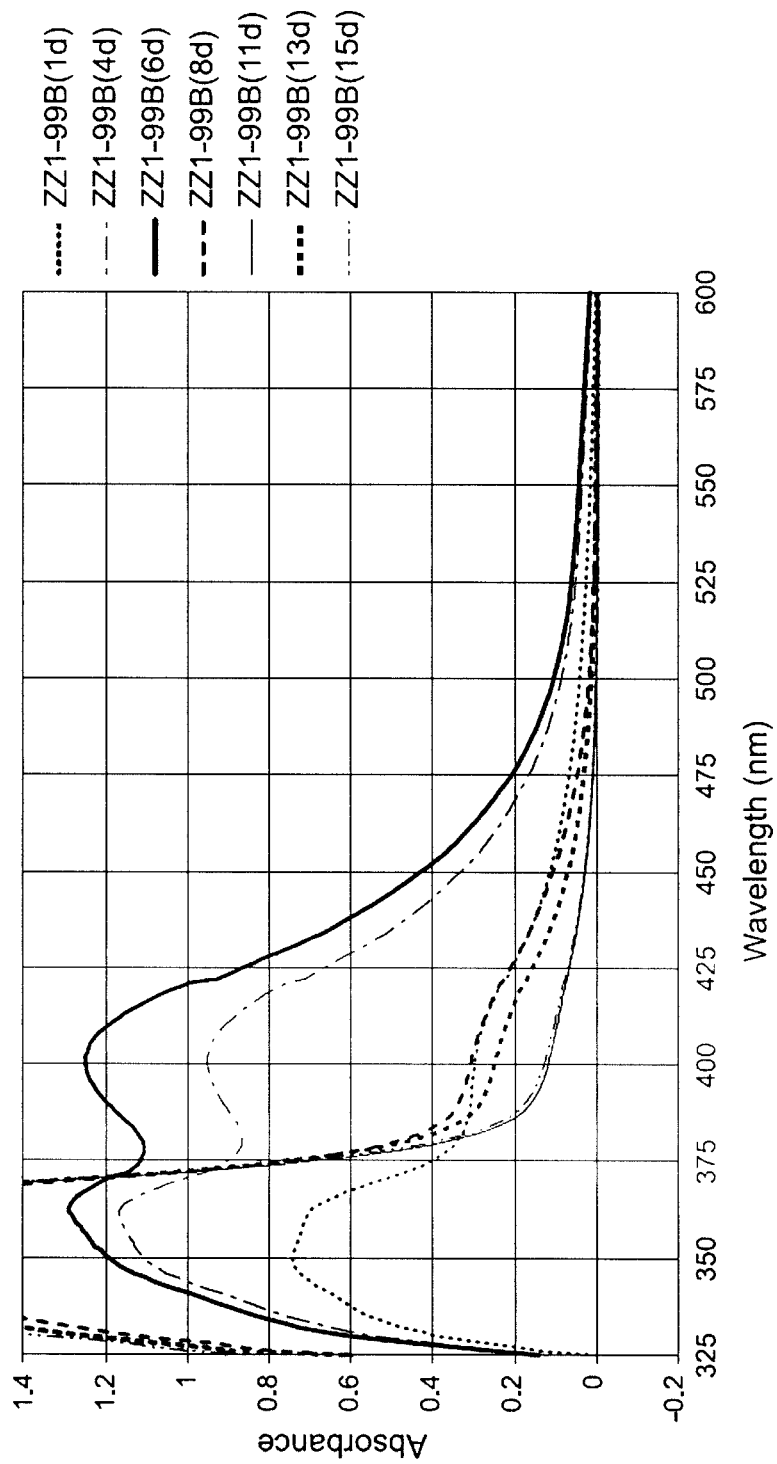
FIG. 7 depicts UV spectra for thermally aged nanogel/MEK Solution ZZ1-99B (@ 40° C., AIBN/0.90%; TEMPO/0.20%, wt/wt of total weight of monomers).

For nanogel ZZ1-99 (UDMA/POEMA (30/70, in MEK), the same reaction system was divided into four portions, in which different amounts of TEMPO was added at 0% wt/wt (ZZ1-99A), 0.20% wt/wt (ZZ1-99B), 0.16% wt/wt (ZZ1-99C) and 0.12% (ZZ1-99D) wt/wt. Then, a post polymerization thermal aging was proceeded at 40° C. for various days (as depicted in FIG. 6 and FIG. 7). The aged solutions were monitored from physical appearance, color change and solution viscosity. As depicted in Table III and FIG. 7, macrogel was formed for the system without any TEMPO addition, and others appears fine. However, it was further noticed that higher viscosity was developed upon further aging at 40° C. for those systems with high concentration of TEMPO. The least viscosity increase is surprisingly found from the nanogel solution with the lowest TEMPO (ZZ1-99D, 0.12% of TEMPO). The general mechanism for side reaction in methacrylate-nitroxide system is illustrated in FIG. 3 (Macromol. Rapid Commun. 2015, 36(13): 1227-1247). A possible side reaction might occur for nanogel/TEMPO solution at elevated temperatures (40-80° C. for MEK system and up to 100° C. for other solvent like toluene) when aged as illustrated in FIG. 4.

TABLE III

Thermal Aging Effect on Solution Viscosity of TEMPO-stabilized Nanogel in MEK

| Nanogel | ZZ1-99A AIBN: 0.45 g TEMPO: 0 | ZZ1-99B AIBN: 0.42 g TEMPO: 0.103 g/0.20% | ZZ1-99C AIBN: 0.41 g TEMPO: 0.075 g/0.16% | ZZ1-99D ABIN: 0.38 g TEMPO: 0.051 g/0.12% |
|---|---|---|---|---|
| As-aged Day@40° C. 0 by Brookfield | 6 | 5 | 6 | 5 |
| As-aged Day@40° C. 1 by Brookfield | 8 | 6 | 6 | 6 |
| As-aged Day@40° C. 5 by Rheometer | 9.0 Gelled | 5.7 | 5.6 | 6.2 |
| As-aged Day@40° C. 6 by Rheometer | 10.7 Gelled | 6.5 | 6.4 | 6.3 |
| As-aged Day@40° C. 7 by Rheometer | 10.2 Gelled | 5.8 | 5.7 | 6.8 |
| As-aged Day@40° C. 8 by Rheometer | 10.8 Gelled | 7.0 | 5.9 | 8.5 |

TABLE III-continued

Thermal Aging Effect on Solution Viscosity of TEMPO-stabilized Nanogel in MEK

| Nanogel | ZZ1-99A<br>AIBN: 0.45 g<br>TEMPO: 0 | ZZ1-99B<br>AIBN: 0.42 g<br>TEMPO:<br>0.103 g/0.20% | ZZ1-99C<br>AIBN: 0.41 g<br>TEMPO:<br>0.075 g/0.16% | ZZ1-99D<br>ABIN: 0.38 g<br>TEMPO:<br>0.051 g/0.12% |
|---|---|---|---|---|
| As-aged Day@40° C. 11 by Rheometer | 9.7 Gelled | 28.7 | 13.5 | 8.6 |
| As-aged Day@40° C. 12 by Rheometer | N/A | 30.0 | 13.5 | 8.6 |
| As-aged Day@40° C. 13 by Rheometer | N/A | 28.7 | 13.5 | 8.6 |
| As-aged Day@40° C. 15 by Rheometer | N/A | 31.6 | 14.6 | 10.6 |

For Hexane-soluble fractions in TEMPO-stabilized nanogel processes, the following was observed:

(i) For UDMA/POEMA (25/75, in MEK): 40.08 (33.5% wt./wt.) of hexane-soluble liquid was collected as POEG/PODEG, unreacted POEMA, POEMA oligomers and free DDT. Little of UDMA and no crystalline residue was present.

(ii) For UDMA/POEMA (30/70, ZZ1-99B; ZZ1-99C; ZZ1-99D in MEK and TEMPO@BRT then aged 15 d 40° C.: 21.5 g (18.9% wt./wt.) of hexane-soluble liquid was collected as POEG/PODEG, unreacted POEMA, POEMA oligomers and free DDT. Little of UDMA but lots of crystalline residue was present.

(iii) For UDMA/POEMA (30/70, ZZ1-127A in MEK) and TEMPO@RT w/o aging: 31.0 g (28% wt./wt.) of hexane-soluble liquid was collected as POEG/PODEG, unreacted POEMA, POEMA oligomers and free DDT. Very little of UDMA and no crystalline residue was present.
  (a) It was estimated based $^1$H NMR there is 14.5 g (46.8%) as free DDT; 13.1 g (42.2%) as free POEMA and 3.4 g (11.0%) of POEMA oligomer.
  (b) 14.5/19.1=76% wt./wt. of DDT was recovered; (13.1+3.4)/47.1=35% wt./wt. of POEMA was recovered.
  (c) Thus, final composition of this nanogel would be as UDMA/POEMA in 39/61 (mol/mol).

(iv) For UDMA/POEMA (30/70, ZZ1-127B in MEK) and TEMPO@RT then aged 7 d RT: 26.9 g (27% wt./wt.) of hexane-soluble liquid was collected as POEG/PODEG, unreacted POEMA, POEMA oligomers and free DDT. Little of UDMA and tiny crystalline residue was present.

(v) For UDMA/BZMA (30/70, ZZ1-130A in MEK) and TEMPO@RT w/o aging: 38.8 g (36% wt./wt.) of hexane-soluble liquid was collected as unreacted BZMA, BZMA oligomers and free DDT. Little of UDMA and no crystalline residue was present.

(vi) For UDMA/BZMA (30/70, ZZ1-130B in MEK) and TEMPO@RT then aged 7 d RT: 33.2 g (34% wt./wt.) of hexane-soluble liquid was collected as unreacted BZMA, BZMA oligomers and free DDT. Little of UDMA and no crystalline residue was present.

Figure 5:
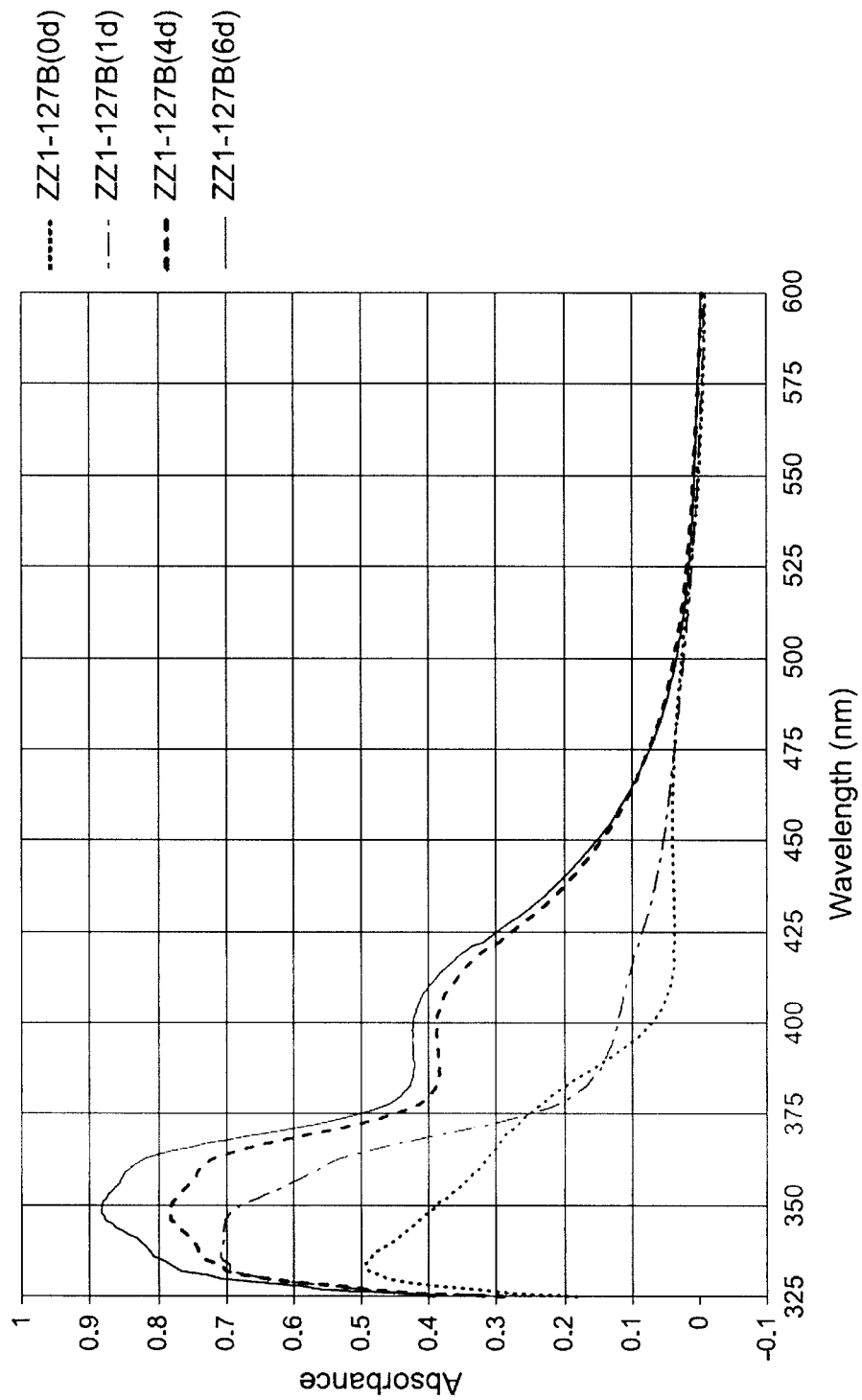
FIG. 5 shows aging@RT Effects on UV Spectra of TEMPO-stabilized methyl ethyl ketone (MEK) solution of UDMA/POEMA nanogel/ZZ1-127B (TEMPO 0.20% wt/wt of total weight of monomers).

For nanogel ZZ1-127 B (UDMA/POEMA (30/70, in MEK), 0.20% wt/wt of TEMPO was added. Then, a post polymerization aging was proceeded at room temperature for various days (as depicted in FIG. 5).

In addition, it should also be pointed out other consequence for TEMPO-dosing at elevated temperature or TEMPO-dosing at room temperature, but further aging at elevated temperature afterward, could lead to further side reactions, which would jeopardize the purpose the effectively stabilize the nanogel.

Finally as shown in Table IV, steady total yield of approx. 77% could be achieved for such a TEMPO-stabilized UDMA/POEMA nanogel system. On the other hand, it was also found that total yield of nanogel (~66%) could not be improved by simply switching to a monomethacrylate with high purity (99.5% of BZMA).

TABLE IV

TEMPO Effect on Yield and Solubility of Nanogel via Batch Process

| | Resin Composition | | | Reaction Condition | | | | Nanogel | |
|---|---|---|---|---|---|---|---|---|---|
| Nanogel | UDMA mol % | BZMA mol % (99.5%) | POEMA mol % (83.0%) | Solvent | Temp. ° C. | Time min | MA Conversion % | Yield of Nanogel % | Solubility in Acetone |
| 200 g ZZ1-85 | Aldrich 30 | 0 | Aldrich 70 | MEK | 80 | 35 + 30 | TEMPO@80° C. 75-85 | N/A | All gelled after aged at 3 days@45° C. |
| 200 g ZZ1-99 | Esstech 30 | 0 | Aldrich 70 | MEK | 80 | 40 | Var TEMPO@RT then aged@40° C. 72, 87-94 | A: N/A<br>B: 85<br>C: 78<br>D2: 82<br>D1: 70<br>D2: 72 | only A got gelled@3 d 40° C. Yes/hazy w/ crystal Insoluble in Acetone but all soluble in MC |

TABLE IV-continued

TEMPO Effect on Yield and Solubility of Nanogel via Batch Process

| | Resin Composition | | | | | | | Nanogel | |
| | | BZMA | POEMA | Reaction Condition | | | | | Solubility |
| Nanogel | UDMA mol % | mol % (99.5%) | mol % (83.0%) | Solvent | Temp. °C. | Time min | MA Conversion % | Yield of Nanogel % | in Acetone |
|---|---|---|---|---|---|---|---|---|---|
| 200 g ZZ1-127 | Aldrich 30 | 0 | Aldrich 70 | MEK | 80 | 40 | TEMPO@RT then precipitated or aged@RT 79 | A: 76 B: 78 | Yes w/o crystal all soluble in Acetone |
| 200 g ZZ1-130 | Aldrich 30 | Aldrich 70 | 0 | MEK | 80 | 40 | TEMPO@RT then precipitated or aged@RT 81 | A: 66 B: 67 | Yes w/o crystal all soluble in Acetone |

For TEMPO-stabilized UDMA/POEMA/DDT/MEK nanogel process following was observed.
(i) Both TEMPO-quenching at elevated temperature or further thermal aging at elevated temperature could trigger side reaction of TEMPO/Methacrylate radicals, which is responsible for the formation of floater (a side reaction from TEMPO related) in MEK solution. Thus TEMPO-quenching at ambient temperature is recommended.
(ii) 10-15%, wt./wt., of TEMPO based on AIBN used in nanogel would be effective for chemically quenching nanogel growing radicals. This would result in a stabilized nanogel for easy following workup process without macro-gelation. This is evident by the fact that the completely soluble nanogel could be recovered from post-vacuum drying process.
(iii) It is recommended that such chemical quenching should not be proceeded at an elevated temperature (80° C.). Instead directly quench the nanogel solution as discharged, once the desire conversion (75%) reached. Additional aging at RT afterwards will not cause any negative impact on the stability and no crystalline by-products would be developed in both nanogel and nanogel residue.

Preparation Example 2: Nanogel Containing 8 Mol % of Trivinyl Crosslinker 306.8 g (1.488 mol) of ethylene glycol phenyl ether methacrylate (POEMA), 55.2 g (0.1632 mol) trimethylolpropane trimethacrylate (TMPTMA), 180.0 g (0.3825 mol) bis-(2-methacryloylethyl)-N,N'-1,9-nonylene biscarbamate (UDMA), 5.4 g (0.033 mol) 2,2-azobis-(2-Methylpropionnitrile) (AIBN) and 123.9 g (0.612 mol) dodecanethiol (DDT) were dissolved in 1084.0 g methylisobutylketone (MIBK). The solution was then pumped through a Fluitec contiplant continuous flow reactor at a flow rate of 4 mL/min at 100° C. The resulting product solution was then quenched by drippling into 0.54 g of predissolved 2,2,6,6-tetramethyl-piperidin-1-oxyl (TEMPO) which was placed in an Ice-bath. The obtained crude product was then dialyzed against acetone for 8 days, using a regenerated cellulose membrane with a molecular weight cutoff (MWCO) of 10 kDa. The purified product was then evaporated under reduced pressure and dried under vacuum.

Figure 8:
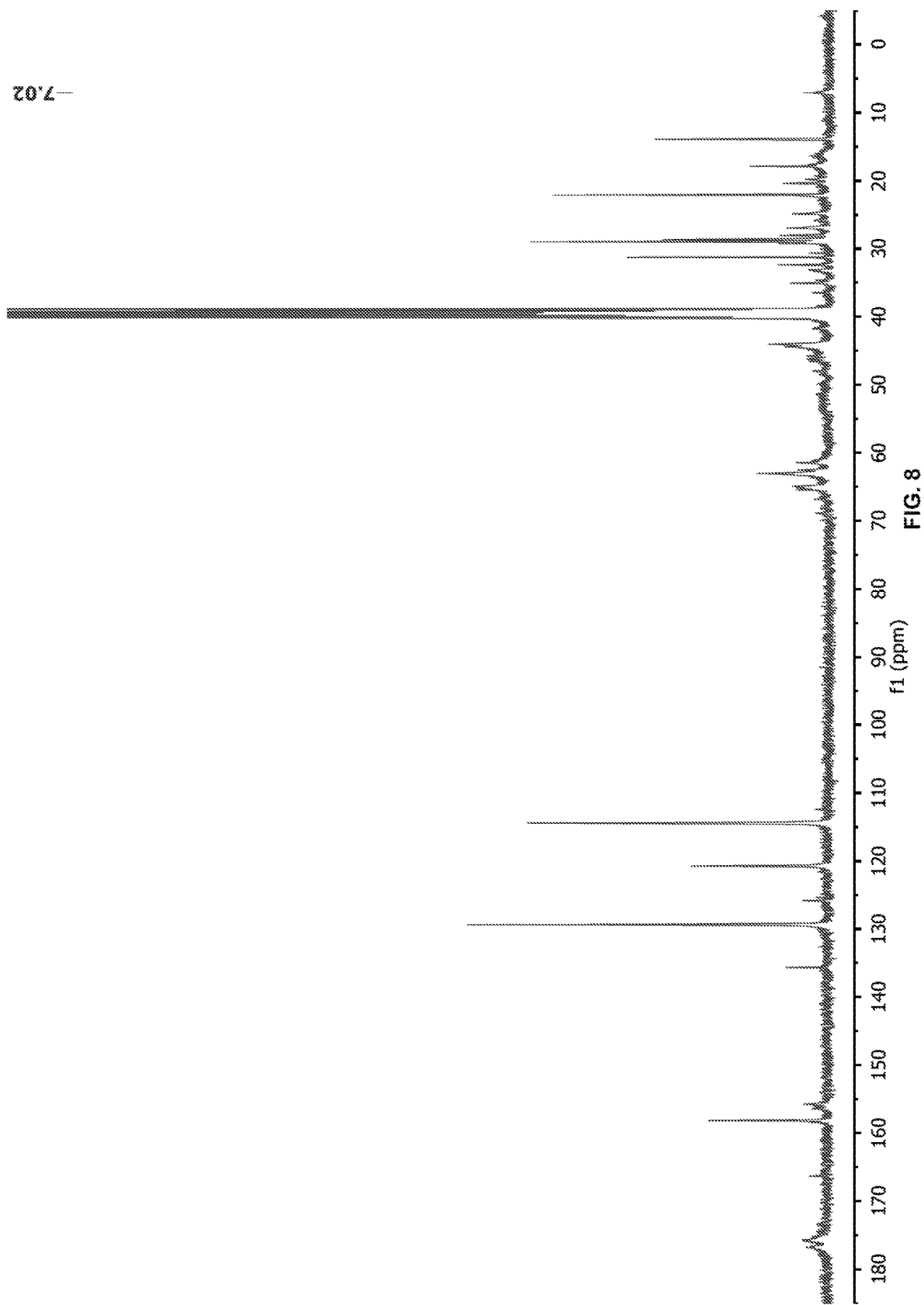
FIG. 8 shows $^{13}$C NMR of nanogel containing TMPTMA crosslinker [DMSO-d6] with characteristic peak at 7.02 ppm.

The product was subsequently analyzed using $^{13}C$-NMR. The —$CH_3$ peak at 7.02 ppm (FIG. 8) is descriptive for the used trifunctional crosslinker and proves successful incorporation into the nanogel.

Preparation Examples 3, 4, 5: Nanogels Containing 15 Mol %, 20 Mol % or 25 Mol % Trivinyl Crosslinker Ethylene glycol phenyl ether methacrylate (POEMA), trimethylolpropane trimethacrylate (TMPTMA), bis-(2-methacryloylethyl)-N, N'-1,9-nonylene biscarbamate (UDMA), 2,2-azobis-(2-methylpropionnitrile) (AIBN) and dodecanethiol (DDT) were dissolved in methylisobutylketone (MIBK). The solution was then pumped through a Fluitec contiplant continuous flow reactor at a flow rate of 4 mL/min at 100° C. The resulting crude product solution was then quenched by drippling into 0.1 g of predissolved 2,2,6,6-tetramethyl-piperidin-1-oxyl (TEMPO) which was placed in an ice-bath. The obtained crude product was dialyzed against acetone for 10 days, using a regenerated cellulose membrane with a molecular weight cutoff (MWCO) of 10 kDa. The purified product was then evaporated under reduced pressure and dried under vacuum.

Table V gives an overview about the used amount of reagents for the synthesis of nanogels containing 15 mol %, 20 mol % or 25 mol % trivinyl crosslinker.

TABLE V

Presentation of the used amount of reagents for the synthesis of nanogels containing 15 mol %, 20 mol % or 25 mol % trivinyl crosslinker

| | 15 mol % TMPTMA | | 20 mol % TMPTMA | | 25 mol % TMPTMA | |
| Reagents | m [g] | n [mol] | m [g] | n [mol] | m [g] | n [mol] |
|---|---|---|---|---|---|---|
| POEMA | 50.33 | 0.244 | 51.52 | 0.250 | 52.77 | 0.256 |
| TMPTMA | 17.70 | 0.052 | 24.15 | 0.071 | 30.92 | 0.091 |
| UDMA | 24.61 | 0.052 | 16.79 | 0.036 | 8.60 | 0.018 |
| AIBN | 0.93 | 0.006 | 0.92 | 0.006 | 0.92 | 0.006 |
| DDT | 21.17 | 0.105 | 21.67 | 0.107 | 22.19 | 0.110 |
| MIBK | 185.27 | | 184.94 | | 184.59 | |
| TEMPO | 0.1 | 0.001 | 0.1 | 0.001 | 0.1 | 0.001 |

Figure 9:
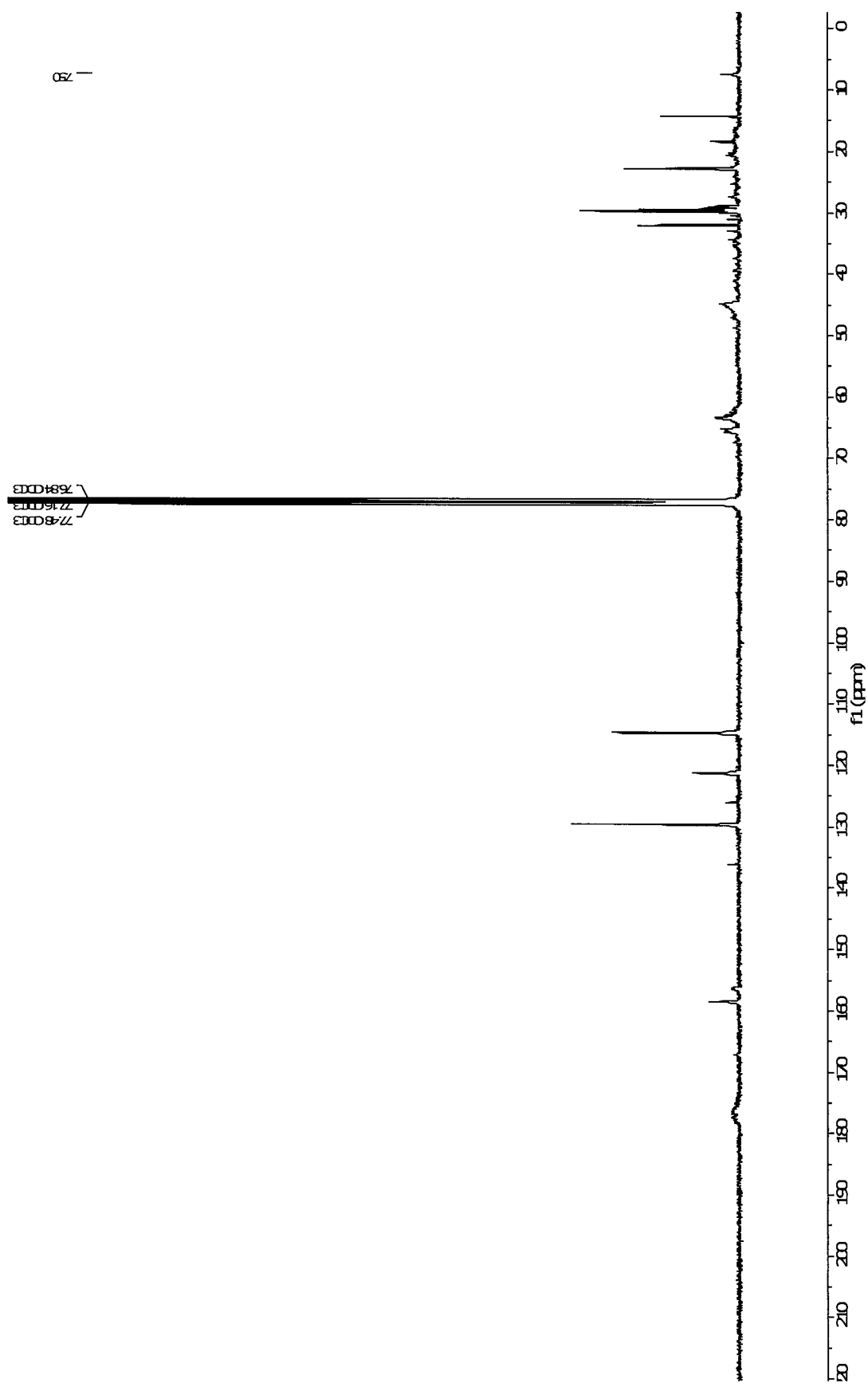
FIG. 9 depicts $^{13}$C-NMR of nanogel containing 15 mol % TMPTMA crosslinker with characteristic peak at 7.50 ppm in $CDCl_3$.
Figure 10:
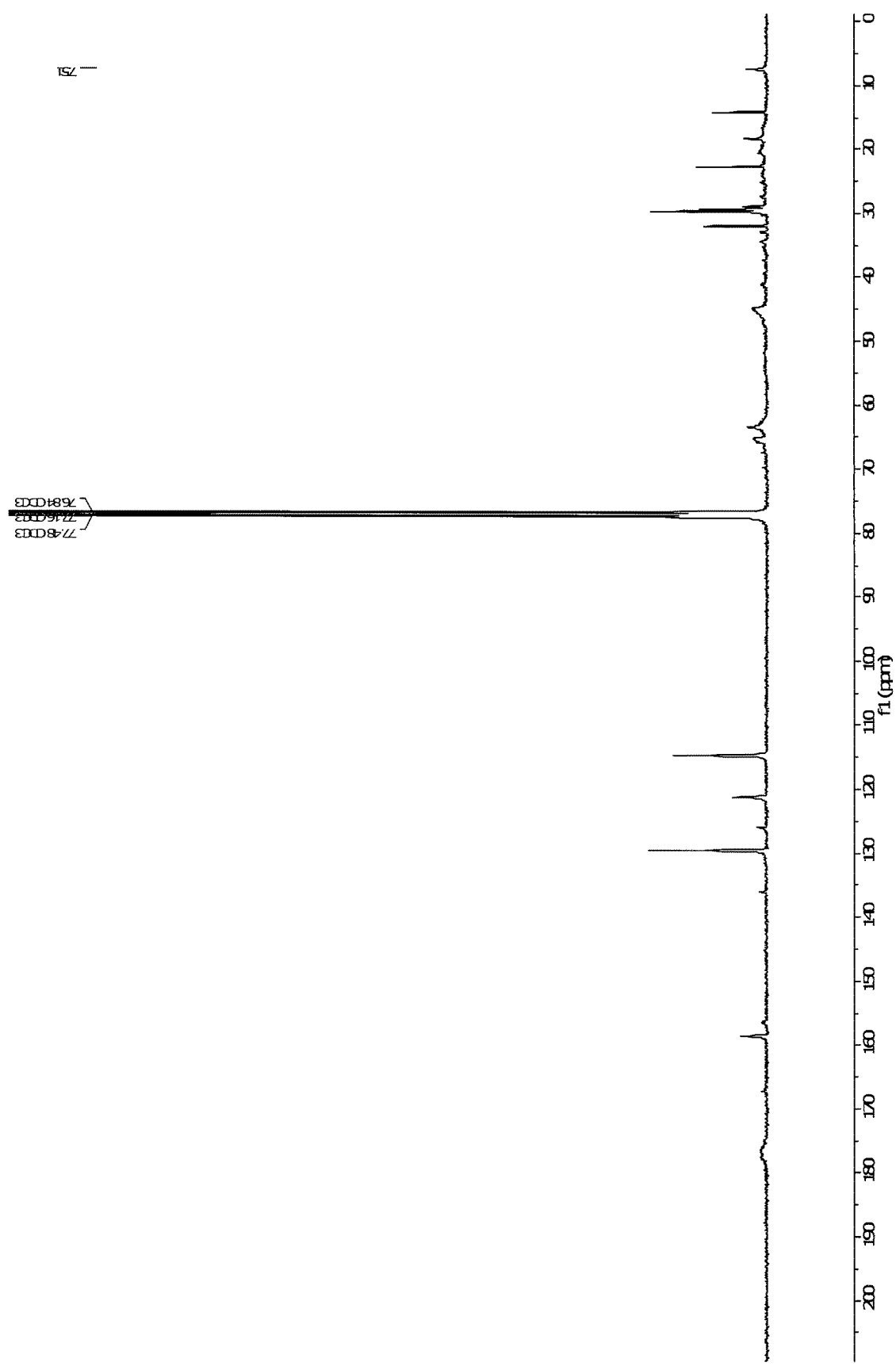
FIG. 10 shows $^{13}$C-NMR of nanogel containing 20 mol % TMPTMA crosslinker with characteristic peak at 7.51 ppm in $CDCl_3$.
Figure 11:
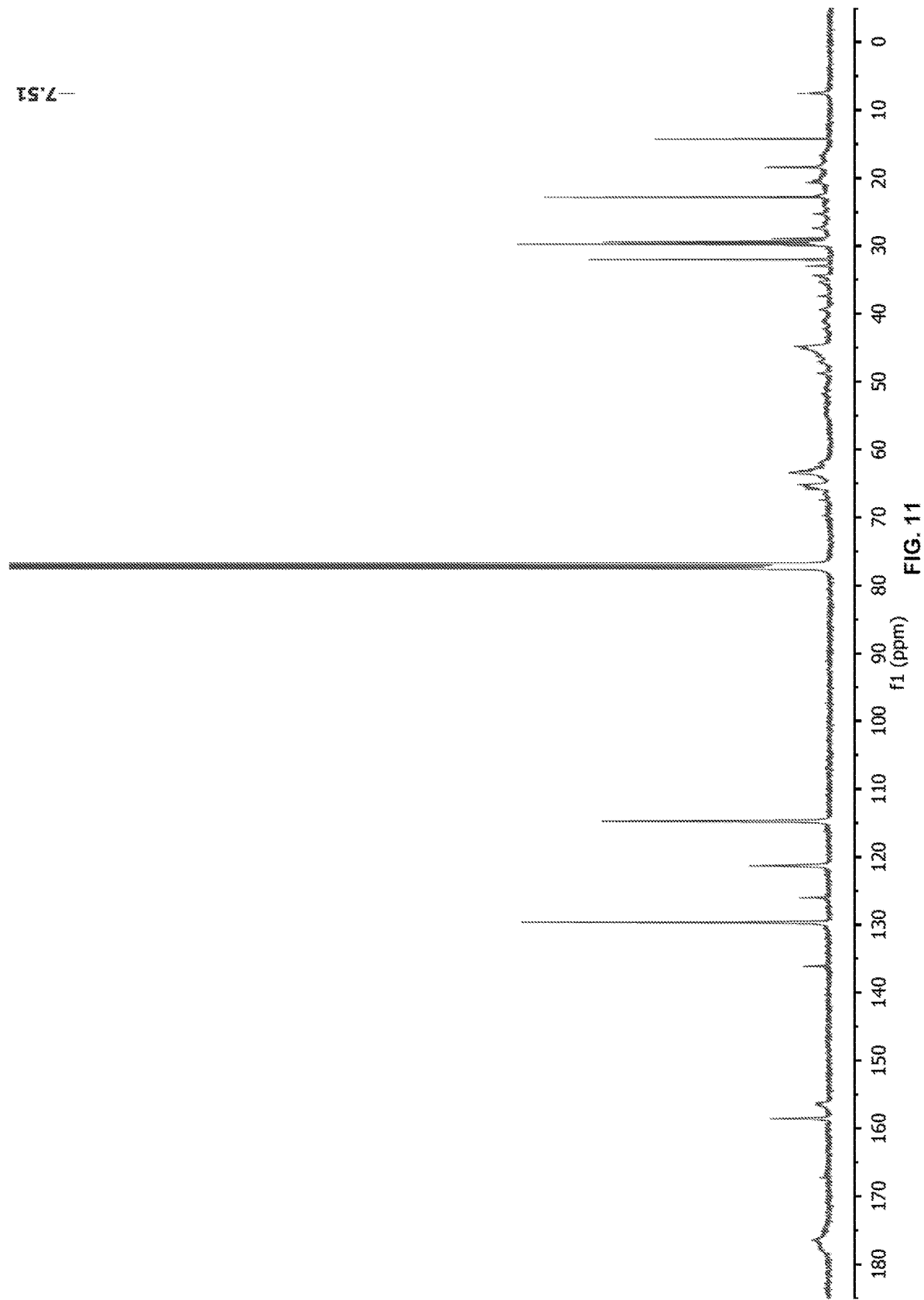
FIG. 11 depicts $^{13}$C-NMR of nanogel containing 25 mol % TMPTMA crosslinker with characteristic peak at 7.50 ppm in $CDCl_3$.

The nanogels were subsequently analyzed using $^{13}C$-NMR. The $CH_3$ peak at 7.50-7.51 ppm (FIG. 9, 10, 11) is descriptive for the used trifunctional crosslinker and proves the successful incorporation of TMPTMA into each nanogel.

Preparation Examples 6: Nanogels Containing 30 Mol % Divinyl-Diallyl-Monoalkene Crosslinker 34.00 g (0.165 mol) Ethylene glycol phenyl ether methacrylate (POEMA), 9.39 g (0.071 mol) N,N'-Bisacryloyl-N, N'-bisallyl-1,4-but-2-endiamine (BAABE), 0.53 g (0.003 mol) 2,2-azobis-(2-methylpropionnitril) (AIBN) and 14.30 g (0.071 mol) dodecanethiol (DDT) were dissolved in 106.78 mL methylisobutylketone (MIBK) in a 250 mL round bottom flask. The reaction take place for 110 min at 80° C. The resulting crude product solution was then quenched by placing in a liquid nitrogen bath. The obtained crude product was dialyzed against acetone for 19 days, using a regenerated cellulose membrane with a molecular weight cutoff (MWCO) of 10 kDa. The purified product was then evaporated under reduced pressure and dried under vacuum.

Figure 12:
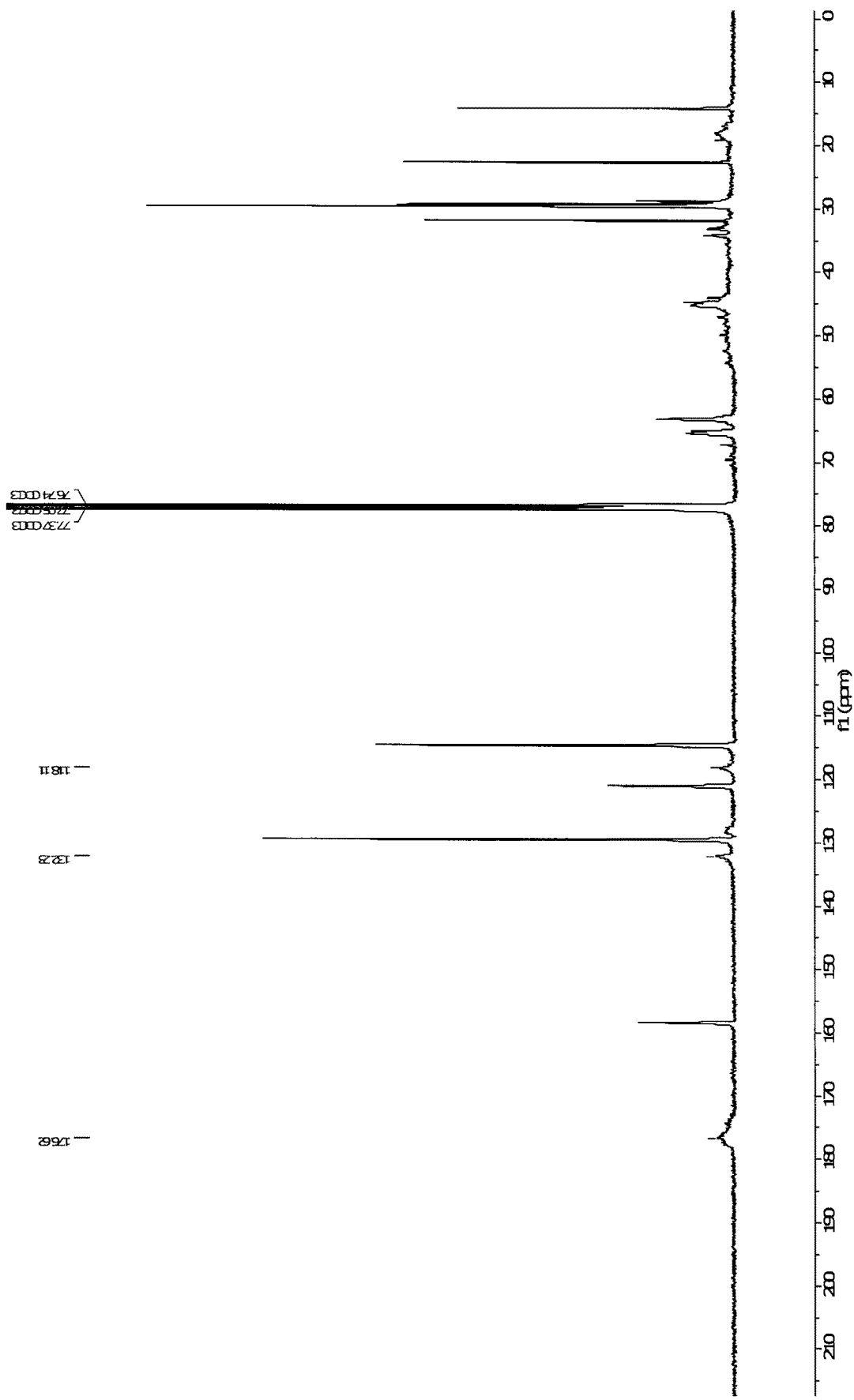
FIG. 12 shows UC-NMR of nanogel containing 30 mol % BAABE crosslinker and 70 mol % POEMA with characteristic peaks at 118.11, 132.23 and 176.62 ppm in $CDCl_3$.

The product was subsequently analyzed using UC-NMR. Representing BAABE peaks are of $CH_2$— from the acryl-groups at 118.11 ppm and of —CH— of the allyl groups at 132.23 ppm (FIG. 12). A representing POEMA peak is the aromatic carbons at 176.62 ppm. These peaks descriptive the composition of the used pentafunctional crosslinker and POEMA and proves the successful incorporation both into the nanogel.

Application Example 1

TEMPO-quenched nanogel that incorporated 8 mol % TMPTMA in the feeding composition were dispersed into Ceram.x Universal Resin at 10 wt % loading level, and was compared to the nanogel without TMPTMA (POEMA/UDMA only). As shown in Table VI, the resin with nanogel containing 8 mol % TMPTMA also can be dispersed well into Ceram.x Universal Resin, resulting in similar viscosity and refractive index. Furthermore, comparable flexural strength and flexural modulus were found as compared to POEMA/UDMA only nanogel, and Ceram.x Universal control resin. More importantly, significant shrinkage stress reduction was observed, with only 10 wt % nanogel loading.

TABLE VI

Properties of Ceram.x Universal Resin dispersed with Nanogel containing 8 mol % of TMPTMA vs. without TMPTMA

| | Resin Mixture | | |
|---|---|---|---|
| | Ceram.x Universal Resin | HLU17-196R1-USCMX (Ceram.x Universal Resin/JBR4-107-01 = 90/10 wt) Nanogel | HLU-198R2-T8CMX (Ceram. X Universal Resin/JBR4-103-01 = 90/10 wt) |
| | None | POEMA/UDMA = 70/30 mol; (MIBK/100° C.; Res t = 12'; DC = 81%) | POEMA/UDMA/TMPTMA = 70/22/8 mol; (MIBK/100° C.; Res t = 12'; DC = 80%) |
| TMPTMA Conc. In Nanogel's Monomer Mixture (POEMA/UDMA/TMPTMA) (Mol %) | 0 | 0 | 8 |
| Nanogel conc. In resin mixture (wt %) | 0 | 10 | 10 |
| 25° C. Viscosity (Pa · S) | 7.4 | 21.0 | 20.6 |
| Refractive Index (25° C.) | 1.518 | 1.519 | 1.519 |
| Flexural Strength (FS, MPa) | 108 (4) | 106 (3) | 106 (2) |
| Flexural Modulus (FM, MPa) | 2457 (62) | 2373 (26) | 2461 (60) |
| Shrinkage Stress (SS, MPa) | 3.94 (0.11) | 2.99 (0.08) | 3.05 (0.18) |
| SS Reduction vs. Ceram.x Universal Resin | — | 24% | 23% |

Application Example 2

TEMPO-quenched nanogel that incorporated 15 mol %, 20 mol % or 25 mol % TMPTMA or 30 mol % BABBE in the feeding composition were dispersed into Ceram.x Universal Resin at 10 wt % loading level. Properties of Ceram.x Universal Resin dispersed with Nanogel containing 15 mol %, 20 mol % or 25 mol % TMPTMA or 30 mol % BABBE are shown in Table VII.

TABLE VII

Properties of Ceram.x Universal Resin dispersed with Nanogel containing 15 mol %, 20 mol % or 25 mol % TMPTMA or 30 mol % BAABE

| | Resin Mixture | | | |
|---|---|---|---|---|
| | HLU18_99R1_TMA15 | HLU18_99R2_TMA20 | HLU18_99R3_TMA25 | HLU18-81R3_BAA3D |
| | | | Nanogel | |
| | POEMA/UDMA/TMPTMA = 70/15/15; (PFR/MIBK/100° C.; DC = 88%) | POEMA/UDMA/TMPTMA = 70/10/20; (PFR/MIBK/100° C.; DC = 81%) | POEMA/UDMA/TMPTMA = 70/5/25; (PFR/MIBK/100° C.; DC = 85%) | POEMA/BAABE = 70/30; (Batch/MIBK/100° C.; DC = 85%) |
| TMPTMA or BAABE conc. In Nanogel's Monomer Mixture | 15 | 15 | 15 | 30 |

TABLE VII-continued

Properties of Ceram.x Universal Resin dispersed with Nanogel containing 15 mol %, 20 mol % or 25 mol % TMPTMA or 30 mol % BAABE

| | Resin Mixture | | | |
|---|---|---|---|---|
| | HLU18_99R1_TMA15 | HLU18_99R2_TMA20 | HLU18_99R3_TMA25 | HLU18-81R3_BAA3D |
| | Nanogel | | | |
| | POEMA/UDMA/TMPTMA = 70/15/15; (PFR/MIBK/100° C.; DC = 88%) | POEMA/UDMA/TMPTMA = 70/10/20; (PFR/MIBK/100° C.; DC = 81%) | POEMA/UDMA/TMPTMA = 70/5/25; (PFR/MIBK/100° C.; DC = 85%) | POEMA/BAABE = 70/30; (Batch/MIBK/100° C.; DC = 85%) |
| (POEMA/UDMA/TMPTMA or BAABE) (mol %) | | | | |
| Nanogel conc. In resin mixture (wt %) | 10 | 10 | 10 | 10 |
| 25° C. Viscosity (Pa · S) | 23.3 | 23.0 | 23.5 | 17.4 |
| RI (25° C.) | 1.5198 | 1.5197 | 1.5198 | — |
| Flexural Strength (FS, MPa) | 107 (3) | 106 (1) | 105 (4) | 104 (1) |
| Flexural Modulus (FM, MPa) | 2463 (106) | 2392 (45) | 2457 (30) | 2383 (62) |
| Shrinkage Stress (SS, MPa) | 3.07 (0.09) | 2.82 (0.19) | 3.09 (0.05) | — |
| SS Reduction vs. Ceram.x Universal Resin | 27% | 33% | 27% | — |

Our previous studies found for nanogel-modified Prime & Bond NT, enhanced shear bond strength (SBS) to dentin after 5,000 and 10,000 cycles of thermocycling. Also, no significant changes were observed for Prime & Bond NT after 6-month water storage at 37° C., however for nanogel-modified Prime & Bond NT, a higher SBS to dentin & enamel after 6-Month water storage at 37° C. was observed.

While the present disclosure has been described with reference to one or more embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. In addition, all numerical values identified in the detailed description shall be interpreted as though the precise and approximate values are both expressly identified.

The invention claimed is:

1. A dental composition comprising a nanogel formed by a process comprising the steps of:
   (a) polymerizing by a thermal polymerization a mixture comprising
      (i) at least one comonomer having one ethylenically unsaturated group,
      (ii) at least one of a comonomer having two ethylenically unsaturated group and at least one comonomer having at least three ethylenically unsaturated groups,
      (iii) at least one chain transfer agent, and
      (iv) an initiator;
   at a reaction temperature to obtain a nanogel solution; and
   (b) terminating the polymerization by lowering the reaction temperature and quenching the nanogel solution with a radical scavenger; wherein the radical scavenger is present at a concentration such that nanogel solution has a thermal stability at storage for 7 days at 25° C.

2. The dental composition according to claim 1, wherein the mixture further comprises a solvent.

3. The dental composition according to claim 1, wherein radical scavenger is present in at least 0.1% wt/wt based on total weight of comonomers in the mixture.

4. The dental composition according to claim 1, wherein the radical scavenger in step (b) is TEMPO, substituted TEMPO, polychlorinated triphenylmethyl radicals, phenalenyls, cyclopentadienyls, other carbon centered radicals, a nitroxide radical, di-tert-alkyliminoxyls, delocalized radicals containing a hydrazyl unit, metal-coordinated phenoxy radicals, stable radicals containing a thiazyl unit or stable radicals of a heavy p-block elements.

5. The dental composition according to claim 4, wherein the radical scavenger is TEMPO.

6. The dental composition according to claim 1, wherein the comonomer having one ethylenically unsaturated group is selected from the group consisting of $C_1$-$C_{12}$ alkyl(meth)acrylates, a hydroxyl alkyl(meth)acrylates, allyl ethers, an aromatic (meth)acrylates, vinylether, vinylester, vinylamine, acrylamide, methacrylamide, hydroxyl alkyl acrylamide and hydroxyl alkyl methacrylamide.

7. The dental composition according to claim 1, wherein the comonomer having two ethylenically unsaturated group comprises a compound of Formula I $$X—R—Y \qquad \text{Formula I}$$

wherein,
X is (meth)acryl or (meth)acrylamide moiety;
Y is (meth)acryl, methacrylamide, allyl, vinyl ether, vinyl ester, or vinyl amine moiety;
R is direct bond or an organic moiety;
wherein the organic moiety is an unsubstituted or substituted $C_1$-$C_{18}$ alkylene, unsubstituted or substituted $C_3$-$C_8$ cycloalkylene, unsubstituted or substituted aralkylene, unsubstituted or substituted $C_1$-$C_8$ cycloalkyl-alkylene, unsubstituted or substituted $C_5$-$C_{18}$ arylene or unsubstituted or substituted $C_3$-$C_{18}$ heteroarylene; wherein each unsubstituted or substituted organic moiety may contain at least one of $C_1$-$C_4$ alkylene, 1-4 urethane groups (—NH—(C=O)—O— or —O—(C=O)—NH—), 1-8 oxygen atoms or nitrogen atoms; wherein each substituted organic moiety is substituted with one or more substituent(s) selected from the group consisting of a alkyl, hydroxyl, a thiol group, —COOM, —PO$_3$M, —O—PO$_3$M$_2$ or —SO$_3$M*; wherein M and M* are independent of each other and are hydrogen atom or metal.

8. The dental composition according to claim 1, wherein the comonomer having at least three ethylenically unsaturated groups is selected from the group consisting of trimethylolpropane tri(meth)acrylate, pentaerythritol triacrylate, and pentaerythritol tetra-acrylate, dipentaerythritol hexaacrylate and N,N'-Bisacryloyl-N,N'-bisallyl-1,4-but-2-endiamine.

9. The dental composition according to claim 1, wherein the comonomer includes at least one having at least three ethylenically unsaturated groups is present in a range of from 1 to 30 mole percent based on total moles of comonomers in the mixture.

10. The dental composition according to claim 1, wherein the comonomer having one ethylenically unsaturated group is present in a range of from 50 to 95 mole percent based on total moles of comonomers in the mixture.

11. The dental composition according to claim 1, wherein the comonomer having two ethylenically unsaturated group is present in a range of from 5 to 50 mole percent based on total moles of comonomers in the mixture.

12. The dental composition according to claim 1, wherein the at least one chain transfer agent is RSH, wherein R is a linear or branched alkyl having from 3 to 20 carbon atoms.

13. The dental composition according to claim 1, wherein the at least one chain transfer agent is present in a concentration of from 5 to 50% mol/mol based on total moles of comonomers in the mixture.

14. The dental composition according to claim 1, wherein the initiator is selected from at least one of organic peroxides and azo compounds.

15. The dental composition according to claim 14, wherein the initiator is selected from the group consisting of benzoyl peroxide, 2,2-azobis-(2-methylpropionitrile) and 2,2-azobis-(2-methylbutyronitrile).

16. The dental composition according to claim 1, wherein the initiator is present in a concentration of from 0.5 to 5.0% wt/wt based on total based on total weight of comonomers in the mixture.

17. The dental composition according to claim 1, wherein the nanogel is soluble in at least one solvent selected from the group consisting of methyl ethyl ketone, acetone and toluene.

18. The dental composition according to claim 1, wherein the nanogel is present in concentration of from 5 to 40% wt/wt based on the total weight of the composition.

19. The dental composition according to claim 18, further comprising
(i) at least one filler in a concentration of from 5 to 95% wt/wt based on the total weight of the composition,
(ii) at least one polymerization initiator in a concentration of from 0.05 to 5% wt/wt based on the total weight of the composition.

20. A nanogel formed by a process comprising the steps of:
(a) polymerizing by a thermal polymerization a mixture comprising:
(i) at least one comonomer having one ethylenically unsaturated group
(ii) at least one of a comonomer having two ethylenically unsaturated group and at least one comonomer having at least three ethylenically unsaturated groups
(iii) at least one chain transfer agent, and
(iv) an initiator;
at a reaction temperature to obtain a nanogel solution; and
(b) terminating the polymerization by lowering the reaction temperature and quenching the nanogel solution with a radical scavenger; wherein the radical scavenger is present at concentration such that nanogel solution has a thermal stability at storage for 7 days at 25° C.; wherein the nanogel is essentially free of macrogel.

21. The nanogel according to claim 20, wherein the nanogel has a hydrodynamic radius of from 2 nm to 20 nm.

22. A method of using the nanogel as defined in claim 20, to prepare a dental composition, wherein the dental composition is a dental composite, dental adhesive, dental cements, resin-modified glass ionomers, vanish, sealant, denture materials, composite blocks, and composite inks for dental 3D printing.

23. A method of forming a nanogel, said method comprising:
(a) polymerizing by a thermal polymerization a mixture comprising:
(i) at least one comonomer having one ethylenically unsaturated group
(ii) at least one of a comonomer having two ethylenically unsaturated group and at least one comonomer having at least three ethylenically unsaturated groups
(iii) at least one chain transfer agent,
(iv) an initiator;
at a reaction temperature to obtain a nanogel solution; and
(b) terminating the polymerization by lowering the reaction temperature and quenching the nanogel solution with a radical scavenger to form the nanogel; wherein the radical scavenger is present at concentration such that nanogel solution has a thermal stability at storage for 7 days at 25° C.

24. The method according to claim 23, wherein the mixture further comprises a solvent.

25. The method according to claim 23, wherein said radical scavenger in step (b) is TEMPO, substituted TEMPO and polychlorinated triphenylmethyl radicals, phenalenyls, cyclopentadienyls, and other carbon centered radicals, a nitroxide radical, di-tert-alkyliminoxyls, delocalized radicals containing a hydrazyl unit, metal-coordinated phenoxy radicals, stable radicals containing a thiazyl unit or stable radicals of a heavy p-block elements.

26. The method according to claim 25, wherein the radical scavenger is TEMPO.

27. The method according to claim 23, wherein the thermal polymerization is performed at the reaction temperature of from 60° C. to 120° C.

28. The method according to claim 23, wherein the termination of polymerization is carried out at reaction temperature of from −196° C. to 25° C.

29. The method according to claim 23, wherein radical scavenger is present in at least 0.1% wt/wt based on total weight of comonomers in the mixture.

30. The method according to claim 23, wherein radical scavenger is added to the nanogel solution when 55-85% of the ethylenically unsaturated group in the comonomer mixture have reacted to form the nanogel.

31. The method according to claim 23, wherein the comonomer having one ethylenically unsaturated group is selected from the group consisting of $C_1$-$C_{12}$ alkyl(meth)acrylates, a hydroxyl alkyl(meth)acrylates, allyl ethers, an aromatic (meth)acrylates, vinylether, vinylester, vinylamine, acrylamide, methacrylamide, hydroxyl alkyl acrylamide and hydroxyl alkyl methacrylamide.

32. The method according to claim 23, wherein the comonomer having two ethylenically unsaturated group comprises a compound of Formula I

     Formula I wherein,

X is (meth)acryl or (meth)acrylamide moiety;

Y is (meth)acryl, methacrylamide, allyl, vinyl ether, vinyl ester, or vinyl amine moiety;

R is direct bond or an organic moiety;

wherein the organic moiety is an unsubstituted or substituted $C_1$-$C_{18}$ alkylene, unsubstituted or substituted $C_3$-$C_8$ cycloalkylene, unsubstituted or substituted aralkylene, unsubstituted or substituted $C_1$-$C_8$ cycloalkylalkylene, unsubstituted or substituted $C_5$-$C_{18}$ arylene or unsubstituted or substituted $C_3$-$C_{18}$ heteroarylene; wherein each unsubstituted or substituted organic moiety may contain at least one of $C_1$-$C_4$ alkylene, 1-4 urethane groups (—NH—(C=O)—O— or —O—(C=O)—NH—), 1-8 oxygen atoms or nitrogen atoms; wherein each substituted organic moiety is substituted with one or more substituent(s) selected from the group consisting of a alkyl, hydroxyl, a thiol group, —COOM, —PO$_3$M, —O—PO$_3$M$_2$ or —SO$_3$M*; wherein M and M* are independent of each other and are hydrogen atom or metal.

33. The method according to claim 31, wherein the comonomer having one ethylenically unsaturated group is 2-phenoxyethyl (meth) acrylate or benzyl (meth) acrylate.

34. The method according to claim 32, wherein the comonomer having two ethylenically unsaturated groups is selected from the group consisting of 2,2'-bis [4-(3-methacryloxy-2-hydroxy propoxy)-phenyl] propane (bis-GMA), tetraethyleneglycoldi(meth)acrylate (TEGDMA), and urethane dimethacrylate (UDMA).

35. The method according to claim 23, wherein the comonomer having at least three ethylenically unsaturated groups is selected from the group consisting of trimethylolpropane tri(meth)acrylate, pentaerythritol triacrylate, pentaerythritol tetra-acrylate and N,N'-Bisacryloyl-N,N'-bisallyl-1,4-but-2-endiamine.

36. The method according to claim 23, wherein the comonomer having at least three ethylenically unsaturated groups is present in a range of from 1 to 30 mole percent based on total moles of comonomers in the mixture.

37. The method according to claim 23, wherein the comonomer having one ethylenically unsaturated group is present in a range of from 50 to 95 mole percent based on total moles of the comonomer in the mixture.

38. The method according to claim 23, wherein the comonomer having two ethylenically unsaturated group is present in a range of from 5 to 50 mole percent based on total moles of the comonomer in the mixture.

39. The method according to claim 23, wherein the initiator is present in a concentration of from 0.5 to 5.0 wt/wt of total weight of the comonomer in the mixture.

40. The method according to claim 23, wherein the at least one chain transfer agent is present in a concentration of from 5 to 50% wt/wt based on total moles of comonomers in the mixture.

* * * * *